US011079394B2

(12) United States Patent
Wang et al.

(10) Patent No.: US 11,079,394 B2
(45) Date of Patent: Aug. 3, 2021

(54) DETECTION OF ANGIOPOIETIN-2 AND THROMBOSPONDIN-2 IN CONNECTION WITH DIAGNOSING ACUTE HEART FAILURE

(71) Applicants: Vanderbilt University, Nashville, TN (US); Beth Israel Deaconess Medical Center, Inc., Boston, MA (US)

(72) Inventors: Thomas J. Wang, Nashville, TN (US); Deepak K. Gupta, Nashville, TN (US); Quinn S. Wells, Nashville, TN (US); Robert E. Gerszten, Boston, MA (US)

(73) Assignees: Vanderbilt University, Nashville, TN (US); Beth Israel Deaconess Medical Center, Inc., Boston, MA (US)

( * ) Notice: Subject to any disclaimer, the term of this patent is extended or adjusted under 35 U.S.C. 154(b) by 194 days.

(21) Appl. No.: 16/045,465

(22) Filed: Jul. 25, 2018

(65) Prior Publication Data
US 2019/0033323 A1    Jan. 31, 2019

Related U.S. Application Data

(60) Provisional application No. 62/536,824, filed on Jul. 25, 2017.

(51) Int. Cl.
*G01N 33/68* (2006.01)
(52) U.S. Cl.
CPC . *G01N 33/6893* (2013.01); *G01N 2333/4704* (2013.01); *G01N 2333/515* (2013.01); *G01N 2800/325* (2013.01); *G01N 2800/52* (2013.01); *G01N 2800/7014* (2013.01)
(58) Field of Classification Search
CPC ..... G01N 2333/4704; G01N 2333/515; G01N 2800/32; G01N 2800/325; G01N 2800/52; G01N 2800/7014; G01N 33/68; G01N 33/6893; G01N 33/49
USPC .............................................. 436/63, 86, 93
See application file for complete search history.

(56) References Cited

U.S. PATENT DOCUMENTS

| | | | |
|---|---|---|---|
| 2013/0085079 A1* | 4/2013 | Gill | G01N 33/6893 506/9 |
| 2016/0091499 A1* | 3/2016 | Sterling | G06Q 40/08 506/9 |
| 2018/0188267 A1* | 7/2018 | Sterling | G16B 40/00 |

OTHER PUBLICATIONS

Wells et al. Journal of the American College of Cardiology, vol. 73, No. 17, May 7, 2019, pp. 2195-2205.*
Yancy CW, Jessup M, Bozkurt B, Butler J, Casey DE, Jr., Colvin MM, Drazner MH, Filippatos GS, Fonarow GC, Givertz MM, Hollenberg SM, Lindenfeld J, Masoudi FA, McBride PE, Peterson PN, Stevenson LW and Westlake C. 2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America. Circulation. 2017;136:e137-e161.
Maisel AS, Krishnaswamy P, Nowak RM, et al. Rapid measurement of B-type natriuretic peptide in the emergency diagnosis of heart failure. N. Engl J Med 2002;347:161-7.
Dieplinger B, Gegenhuber A, Haltmayer M and Mueller T. Evaluation of novel biomarkers for the diagnosis of acute destabilised heart failure in patients with shortness of breath. Heart. 2009;95:1508-13.
Van Kimmenade RR, Januzzi JL, Jr., Ellinor PT, Sharma UC, Bakker JA, Low AF, Martinez A, Crijns HJ, MacRae CA, Menheere PP and Pinto YM. Utility of amino-terminal pro-brain natriuretic peptide, galectin-3, and apelin for the evaluation of patients with acute heart failure. J Am Coll Cardiol. 2006;48:1217-24.
Roberts E, Ludman AJ, Dworzynski K, Al-Mohammad A, Cowie MR, McMurray JJ, Mant J and Failure NGDGfAH. The diagnostic accuracy of the natriuretic peptides in heart failure: systematic review and diagnostic meta-analysis in the acute care setting. BMJ. 2015;350:h910.
Benest AV, Kruse K, Savant S, Thomas M, Laib AM, Loos EK, Fiedler U and Augustin HG. Angiopoietin-2 is critical for cytokine-induced vascular leakage. PLoS One. 2013;8:e70459.
Saharinen P, Eklund L, Miettinen J, Wirkkala R, Anisimov A, Winderlich M, Nottebaum A, Vestweber D, Deutsch U, Koh GY, Olsen BR and Alitalo K. Angiopoietins assemble distinct Tie2 signalling complexes in endothelial cell-cell and cell-matrix contacts. Nat Cell Biol. 2008;10:527-37.
Papageorgiou AP, Swinnen M, Vanhoutte D, VandenDriessche T, Chuah M, Lindner D, Verhesen W, de Vries B, D'Hooge J, Lutgens E, Westermann D, Carmeliet P and Heymans S. Thrombospondin-2 prevents cardiac injury and dysfunction in viral myocarditis through the activation of regulatory T-cells. Cardiovascular research. 2012;94:115-24.
Van Almen GC, Swinnen M, Carai P, Verhesen W, Cleutjens JP, D'Hooge J, Verheyen FK, Pinto YM, Schroen B, Carmeliet P and Heymans S. Absence of thrombospondin-2 increases cardiomyocyte damage and matrix disruption in doxorubicin-induced cardiomyopathy. Journal of molecular and cellular cardiology. 2011;51:318-28.
Swinnen M, Vanhoutte D, Van Almen GC, Hamdani N, Schellings MW, D'Hooge J, Van der Velden J, Weaver MS, Sage EH, Bornstein P, Verheyen FK, VandenDriessche T, Chuah MK, Westermann D, Paulus WJ, Van de Werf F, Schroen B, Carmeliet P, Pinto YM and Heymans S. Absence of thrombospondin-2 causes age-related dilated cardiomyopathy. Circulation. 2009;120:1585-97.
Schroen B, Heymans S, Sharma U, Blankesteijn WM, Pokharel S, Cleutjens JP, Porter JG, Evelo CT, Duisters R, van Leeuwen RE, Janssen BJ, Debets JJ, Smits JF, Daemen MJ, Crijns HJ, Bornstein P And Pinto YM. Thrombospondin-2 is essential for myocardial matrix integrity: increased expression identifies failure-prone cardiac hypertrophy. Circulation research. 2004;95:515-22.

(Continued)

*Primary Examiner* — Maureen Wallenhorst
(74) *Attorney, Agent, or Firm* — Stites & Harbison PLLC; Mandy Wilson Decker

(57) ABSTRACT

Methods for detecting angiopoietin-2 (Angpt-2) and/or thrombospondin-2 (Tsp-2) in a sample involve obtaining or having obtained a blood or plasma sample from a subject; and detecting Angpt-2 and Tsp-2 in the sample. Detecting can involve performing an assay to determine whether the sample includes Angpt-2 and/or Tsp-2 or elevated levels of Angpt-2 and/or Tsp-2. Elevated levels are indicative of acute heart failure.

14 Claims, 6 Drawing Sheets

(56) References Cited

OTHER PUBLICATIONS

Poss J, Ukena C, Kindermann I, Ehrlich P, Fuernau G, Ewen S, Mahfoud F, Kriechbaum S, Bohm M and Link A. Angiopoietin-2 and outcome in patients with acute decompensated heart failure. Clinical research in cardiology : official journal of the German Cardiac Society. 2015;104:380-7.

Link A, Poss J, Rbah R, Barth C, Feth L, Selejan S and Bohm M. Circulating angiopoietins and cardiovascular mortality in cardiogenic shock. Eur Heart J. 2013;34:1651-62.

Chong AY, Caine GJ, Freestone B, Blann AD and Lip GY. Plasma angiopoietin-1, angiopoietin-2, and angiopoietin receptor tie-2 levels in congestive heart failure. J Am Coll Cardiol. 2004;43:423-8.

Chen S, Guo L, Chen B, Sun L and Cui M. Association of serum angiopoietin-1, angiopoietin-2 and angiopoietin-2 to angiopoietin-1 ratio with heart failure in patients with acute myocardial infarction. Experimental and therapeutic medicine. 2013;5:937-941.

Hanatani S, Izumiya Y, Takashio S, Kimura Y, Araki S, Rokutanda T, Tsujita K, Yamamoto E, Tanaka T, Yamamuro M, Kojima S, Tayama S, Kaikita K, Hokimoto S and Ogawa H. Circulating thrombospondin-2 reflects disease severity and predicts outcome of heart failure with reduced ejection fraction. Circulation journal : official journal of the Japanese Circulation Society. 2014;78:903-10.

Eleuteri E, Di Stefano A, Tarro Genta F et al. Stepwise increase of angiopoietin-2 serum levels is related to haemodynamic and functional impairment in stable chronic heart failure. Eur J Cardiovasc Prey Rehabil 2011;18:607-14.

Berezin AE, Kremzer AA, Samura TA. Circulating thrombospondine-2 in patients with moderate-to-severe chronic lead failure due to coronary artery disease. J Biomed Res 2015;30.

Eleuteri E, Di Stefano A, Giordano A et al. Prognostic value of angiopoietin-2 in patients with chronic heart failure. Int J Cardiol 2016;212:364-8.

Kimura Y, Izumiya Y, Hanatani S et al. High serum levels of thrombospondin-2 correlate with poor prognosis of patients with heart failure with preserved ejection fraction. Heart Vessels 2016;31:52-9.

* cited by examiner

DETECTION OF ANGIOPOIETIN-2 AND THROMBOSPONDIN-2 IN CONNECTION WITH DIAGNOSING ACUTE HEART FAILURE

RELATED APPLICATIONS

This application claims priority from U.S. Provisional Application Ser. No. 62/536,824 filed Jul. 25, 2017, the entire disclosure of which is incorporated herein by this reference.

GOVERNMENT INTEREST

This invention was made with government support under grant number K12 HL109019, K23 HL128928-01A1, R01HL133870-01A1, R01HL132320-01, and UL1TR000445 awarded by the National Institutes of Health. The government has certain rights in the invention.

TECHNICAL FIELD

The presently-disclosed subject matter generally relates to methods that involve detecting angiopoietin-2 (Angpt-2) and thrombospondin-2 (Tsp-2) in a sample from a subject. The subject can be at risk for acute heart failure or experiencing symptoms that can be caused by multiple conditions, including acute heart failure and other conditions.

INTRODUCTION

Circulating biomarkers can aid diagnosis, risk stratification, and selection of therapies. There has been substantial interest in identifying cardiovascular biomarkers, because cardiovascular diseases can have wide variation in symptoms and signs, disease course, and treatment response. Nonetheless, despite the large number of biomarkers studied, adoption has been slowed by modest specificity and incomplete validation.

Biomarker studies often focus on candidates from a limited number of pathophysiologic pathways.[1, 2] Advances in proteomic technologies have enabled simultaneous interrogation of many proteins, opening the possibility of biomarker discovery at scale and with less constraint by existing knowledge.[3-5] Nonetheless, newer platforms require easy access to large amounts of clinical data and biosamples for discovery and validation. Thus, the time and expense to create clinically-useful biobanks can present significant barriers.

Accordingly, the present inventors developed a methodology linking patient-level electronic health record (EHR) data to an automated system for retrieval of plasma from discarded clinical blood specimens. Coupling EHRs, from which many phenotypes can be extracted, with discarded biospecimens after clinical blood draws provides a pragmatic approach for biobanking. This paradigm has been effective for genetic studies of disease and drug response but has not been extended to plasma protein-based biomarker discovery.[6-11]

Heart failure (HF) is a relapsing and remitting disorder with multiple potential etiologies and a variable disease course. The natriuretic peptides (e.g. B-type natriuretic peptide), are the only FDA approved biomarkers for the diagnosis of acute HF. Although natriuretic peptides have high sensitivity in the acute setting, they have only moderate specificity, such that individuals may have elevated natriuretic peptides levels for reasons other than HF.[12] Furthermore, a variety of non-cardiac factors, including gender, body mass index (BMI), and race/ethnicity, influence circulating BNP levels.[13]

As disclosed herein, the present inventors leveraged EHR data, discarded clinical specimens, and a recently-developed aptamer-based proteomic platform to identify and validate candidate HF biomarkers. The candidate biomarkers were tested in three separate validation cohorts: an emergency department (ED) cohort of patients with suspected acute HF, a community-based cohort of individuals at risk for HF, and a sample of patients undergoing heart transplantation.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Some embodiments of the presently-disclosed subject matter include a method for treating a subject which involve determining whether there is elevated angiopoietin-2 (Angpt-2) and/or thrombospondin-2 (Tsp-2) in a blood or plasma sample from the subject by (i) obtaining or having obtained the blood or plasma sample from the subject, and (ii) performing or having performed an assay to determine whether the sample includes elevated Angpt-2 and/or Tsp-2; and if there is elevated Angpt-2 and/or Tsp-2 in the sample, then administering treatment for acute heart failure to the subject.

In some embodiments, the presently-disclosed subject matter includes a method of diagnosing and treating acute heart failure in a subject, which involves obtaining or having obtained a blood or plasma sample from the subject to detect levels in the sample of one or both of Angpt-2 and Tsp-2; diagnosing the subject with acute heart failure when there is an elevated presence of Angpt-2 and/or Tsp-2 in the sample; and administering treatment for acute heart failure to the diagnosed subject.

In some embodiments, the presently-disclosed subject matter includes a method of monitoring efficacy of a treatment for acute heart failure in a subject, which involves assaying a first blood or plasma sample from the subject to detect a first level of one or both of Angpt-2 and Tsp-2; administering a treatment; determining a second level of the of one or both of Angpt-2 and Tsp-2 in a second blood or plasma sample from the subject obtained after administration of the treatment to the subject; and comparing the first and second levels of Angpt-2 and/or Tsp-2, wherein a decrease in the Angpt-2 and/or Tsp-2 indicates that the treatment has been effective, and an increase or no change indicates that the treatment has not been effective.

In some embodiments, the presently-disclosed subject matter includes a method of detecting a combination of angiopoietin-2 (Angpt-2) and thrombospondin-2 (Tsp-2) in a subject, which involves obtaining or having obtained a blood or plasma sample from the subject, and detecting or having detected Angpt-2 and Tsp-2 in the sample. In some embodiments, the method also involves diagnosing the subject with acute heart failure when there is an elevated presence of Angpt-2 and/or Tsp-2 in the sample. In some embodiments, the method further involves administering treatment for acute heart failure to the subject.

Some embodiments of the methods disclosed herein can also involve detecting natriuretic peptides in the sample. In some embodiments, the natriuretic peptides include one or more of B-type natriuretic peptide (BNP), N-terminal pro-BNP (NTproBNP), and mid-regional proatrial natriuretic peptide (MRproANP). Accordingly, in some embodiments, the methods involve detecting or having detected natriuretic peptides in the sample, and diagnosing the subject with acute heart failure when there is an elevated presence of Angpt-2 and/or Tsp-2, and when the natriuretic peptide levels are above a threshold level for excluding acute heart failure.

In some embodiments, the subject is experiencing dyspnea, and the method can be used to determine whether the symptom is associated with acute heart failure or another condition. When there are elevated levels of Angpt-2 and/or Tsp-2, treatment for acute heart failure can be administered, and treatments for other conditions associated with dyspnea can be avoided, such as administration of antibiotics and intravenous fluids. Treatments for acute heart failure include, for example, administering diuretics.

In some embodiments the method can be used to identifying a subject as having an increased risk of developing heart failure. For example, in some embodiments, the methods can be used to test a subject having an increased risk due to coronary artery disease, myocardial infarction, hypertension, diabetes mellitus, or obesity. In some embodiments, when there are elevated levels of Angpt-2 and/or Tsp-2, treatment is administered to the subject to prevent or delay disease onset. Treatments can be elected, for example, from one or more of more aggressive blood pressure, more aggressive blood lipid goals, more intensive clinical monitoring, more frequent clinical monitoring, and specific lifestyle recommendations (e.g., weight management, exercise, etc.).

In some embodiments, the method includes contacting the sample with an Angpt-2 probe and a Tsp-2 probe, and detecting binding between Angpt-2 and Tsp-2 and the probe. The presently-disclosed subject matter further includes a kit including both an Angpt-2 probe and a Tsp-2 probe.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

CVD=cardiovascular disease, HF=heart failure. NTproBNP values reported as median and interquartile range.

Figure 8:
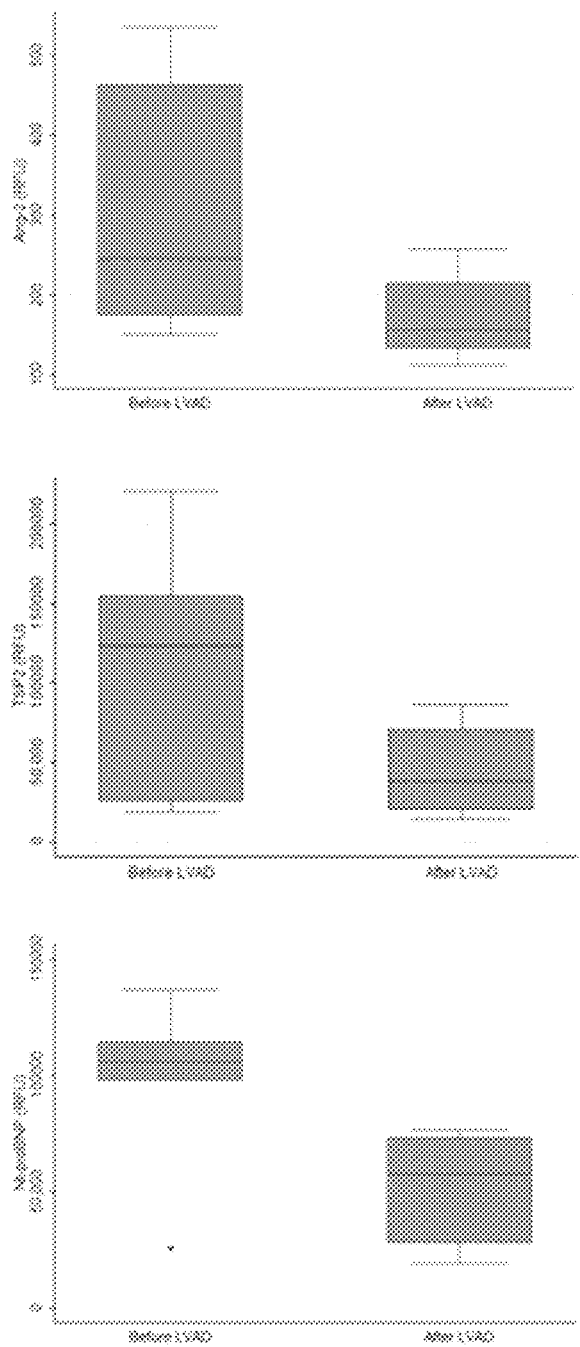

FIG. 8. Angiopoietin-2, thrombospondin-2, and NTproBNP levels in advanced heart failure patients before and after left ventricular assist device. Among advance heart failure patients undergoing left ventricular assist device (LVAD), levels of angiopoietin-2, thrombospondin-2, are reduced after LVAD compared with before LVAD, p=0.04 for both, p=0.08 for NTproBNP. ANGPT2=angiopoietin-2, TSP2=thrombospondin-2, NTproBNP=N-terminal pro B-type natriuretic peptide. RFU=relative fluorescence units.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to methods that involve detecting a angiopoietin-2 (Angpt-2) and thrombospondin-2 (Tsp-2) in a sample from a subject. The subject can be at risk for acute heart failure or experiencing symptoms that can be caused by multiple conditions, including acute heart failure and other conditions.

Heart Failure

Patients presenting to acute care (e.g., emergency department) with dyspnea (shortness of breath) could have any number of conditions. Indeed, subjects with shortness of breath present a diagnostic challenge for providers because this symptom can be caused multiple conditions, such as, for example, heart failure, pneumonia, chronic obstructive pulmonary disease, asthma, and pulmonary embolism. Quickly determining the cause of the patient's symptoms is important because it allows initiation of appropriate treatment and avoidance of ineffective therapies that may expose patients to unnecessary risk. For example, in the acute care setting, identifying individuals whose symptoms are due to acute heart failure would result in treatment with heart failure directed therapies (e.g. diuretics, vasodilators) and potential avoidance of drugs such as antibiotics and intravenous fluids used for treatment of other diagnoses, such as pneumonia.[23,37]

Diuretics are medications that cause sodium and water removal from the body and are recommended as the initial therapy for patients with acute heart failure.[37,38] The critical importance of establishing the diagnosis of acute heart failure and early delivery of diuretics has been demonstrated in several recent studies that have shown worse prognosis resulting from delayed heart failure diagnosis and delayed delivery of diuretics.[38-41] As important may be the avoidance of antibiotics and intravenous fluids in patients with acute heart failure, as these therapies are associated with worse outcomes unless concomitant pneumonia or other infection is present.[42,43]

As disclosed herein, angiopoietin-2 (Angpt-2) and thrombospondin-2 (Tsp-2) were significantly higher in subjects with acute heart failure than in subjects with shortness of breath from another cause. Furthermore, diagnostic accuracy for acute heart failure is significantly improved the presently-disclosed methods that assess Angpt-2 and Tsp-2, as compared to the current diagnostic standard, which measures B-type natriuretic peptides (BNP).

The methods disclosed herein are also useful in the context of ambulatory and community dwelling subjects for use in assessing and identifying those at increased risk for heart failure. A number of chronic medical conditions, including, for example, coronary artery disease, myocardial infarction, hypertension, diabetes mellitus, and obesity increase the risk of developing heart failure.[37] These conditions are very common, such that identifying those individuals at increased heart failure risk could facilitate initiation of measures to prevent or delay disease onset. Such interventions might include, for example, more aggressive blood pressure or blood lipid goals, more intensive or frequent clinical monitoring, or specific lifestyle recommendations (e.g., weight management, exercise, etc.). This approach has been demonstrated to be effective using NTproBNP assessment as a screening tool.[45]

As disclosed herein, angiopoietin-2 and thrombospondin-2 were found to be significantly higher in a group of community dwelling individuals that went on to develop heart failure compared with the group of individuals that did not develop heart failure. Further, the risk of heart failure increased with higher levels of each of Angpt-2 and Tsp-2, and the associations were present even after accounting for clinical features and levels of NTproBNP.

Detection Methods

As noted above, angiopoietin-2 (Angpt-2) and thrombospondin-2 (Tsp-2) were significantly higher in subjects with acute heart failure than in subjects with shortness of breath from another cause. Angpt-2 and Tsp-2 were also found to be significantly higher in a group of community dwelling individuals that went on to develop heart failure as compared with the group of individuals that did not develop heart failure.

The samples used to perform the methods disclosed herein are blood or plasma samples, which can be prepared for testing according to methods known in the art. Exemplary methods are disclosed herein. A number of methods are also known in the art that can be used to assay the samples to detect the presence of levels of Angpt-2 and Tsp-2. Exemplary methods are disclosed herein.

Such detection methods can be used to assess a presence or level of Angpt-2 and/or Tsp-2. As noted herein, an elevated level of Angpt-2 and/or Tsp-2 in a sample from a subject is indicative of the subject having acute heart failure. In some embodiments, a level of Angpt-2 is considered an elevated level when it is at or above about 215, 216, 217, 218, 219, 220, 221, 222, 223, 224, 225, 226, 227, 228, 229, 230, 232, 233, 234, 235, 236, 237, 238, 239, or 240 pg/ml in the sample. In some embodiments, a level of Angpt-2 is considered an elevated level when it is at or above about 500, 1000, 1500, 2000, or 2500 pg/ml. In some embodiments a level of Tsp-2 is considered an elevated level with it is at or above about 25, 26, 27, 28, 29, 30, 31, 32, 33, 34, 35, 36, 37, 38, 39, 40, 41, 42, 43, 44, or 45 ng/ml in the sample. In some embodiments a level of Tsp-2 is considered an elevated level with it is at or above about 50, 100, 150, or 200 ng/ml.

The terms "diagnosing" and "diagnosis" as used herein refer to methods by which the skilled artisan can estimate and even determine whether or not a subject has acute heart failure or a susceptibility or risk of developing heart failure. Making a diagnosis of or excluding to condition or risk do not refer to the ability to predict the course or outcome of the condition with 100% accuracy. Instead, the skilled artisan will understand that the terms refer to an increased (or decreased) probability that a certain course or outcome will occur; that is, that a course or outcome is more likely to occur in a subject diagnosed with acute heart failure, or less likely to occur in a subject for which acute heart failure is excluded. In this regard, diagnosis of acute heart failure includes diagnosis of a high risk of acute heart failure. In some embodiments, a high risk is a probability of at least about 50%, 60%, 70%, 80%, 90%, or greater. Excluding acute heart failure includes a diagnosis of a low risk of acute heart failure. In some embodiments, a low risk is a probability of less than about 50%, 40%, 30%, 20%, 10%, or lower.

"Making a diagnosis" or "diagnosing", as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the presence and/or level of Angpt-2 and/or Tsp-2. Further, in some embodiments of the presently disclosed subject matter, multiple determination of the Angpt-2 and Tsp-2 can be made over time to facilitate diagnosis and/or prognosis. A temporal change can be used to predict a clinical outcome, monitor the progression of the condition or risk and/or efficacy of appropriate therapies directed against the condition. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

Combination Diagnostics

In some embodiments, the methods include performing an additional diagnostic assessment for Acute Heart Failure or to exclude Acute Heart Failure. Currently, the only Food and Drug Administration-approved and American Heart Association/American College of Cardiology guideline-recommended biomarkers for excluding the diagnosis of heart failure are assessment of natriuretic peptides, B-type natriuretic peptide (BNP), N-terminal pro-BNP (NTproBNP), and mid-regional proatrial natriuretic peptide (MRproANP).[23,37] At their recommended diagnostic thresholds, natriuretic peptides are quite sensitive (i.e., able to exclude heart failure as a cause of shortness of breath) but have limited specificity (i.e., ability to positively identify heart failure as a cause of shortness of breath).[44,12] The lack of specificity of natriuretic peptides for acute heart failure is a clinically relevant limitation.[23,37]

Accordingly, in some embodiments of the presently-disclosed methods Angpt-2 and/or Tsp-2 are assayed to positively diagnose acute heart failure, together with a test to assay natriuretic peptides to exclude acute heart failure, thus enhancing the sensitivity and specificity of the overall method. In this regard, further to obtaining a positive result for Angpt-2 and/or Tsp2, a negative result on a natriuretic peptide test can provide further evidence supporting a diagnosis of Acute Heart Failure. Conversely, further to obtaining a negative result for Angpt-2 and/or Tsp2, a positive result on a natriuretic peptide test can provide further evidence supporting an exclusion of Acute Heart Failure.

Based on prior studies, a level of plasma B type natriuretic peptide (BNP) of at or below about 100 ng/L; a level of N terminal probrain natriuretic peptide (NTproBNP) of at or below about 300 ng/L, and/or a level of mid-regional proatrial natriuretic peptide (MRproANP) of at or below about 120 pmol/L is recommended for excluding heart failure in acute care settings such as emergency departments.[12]

In some embodiments of the method, a clinical heart failure (HF) score can also be obtained using Framingham Criteria. As will be understood by one of ordinary skill in the art, Framingham Criteria can be used to determine a clinical heart failure (HF) score. Briefly, the clinical HF score is determined by assessing major and minor criteria, and associating points with each such criteria. Additional information can be found, for example, at framinghamheartstudy.org.

Therefore, the combination of angiopoietin-2 and thrombospodin-2 with natriuretic peptides and clinical information, including a clinical heart failure (HF) score using Framingham Criteria, for example, can facilitate diagnostic accuracy for acute heart failure, which may promote more appropriate and effective treatment.

Methods of Treatment

The methods of the presently-disclosed subject matter can be used to select a treatment for a subject. In some embodiments, the methods can be used to administer treatment to a subject. When a subject has been diagnosed by a method as described herein, the method can involve recommending or administering treatment to the subject.

As will be apparent to the skilled artisan upon studying this document, the recommended or administered treatment will vary depending on the circumstances in which the method is employed. For example, the context of acute care, the recommended or administered treatment for a diagnosed subject would be treatment for acute heart failure. Such treatment could include administering diuretics (e.g., furosemide), oxygen therapy and/or ventilator support, and/or vasodilation.

In the context of a subject identified as having a susceptibility or increased risk for heart failure the recommended or administered treatment would be treatment to prevent or delay onset of the disease. Such interventions might include, for example, more aggressive blood pressure or blood lipid goals, more intensive or frequent clinical monitoring, or specific lifestyle recommendations (e.g., weight management, exercise, etc.).

Additional treatments are known in the art, and are further described in the cited references, the disclosures of which are incorporated by reference.[23,37,38]

As used herein, the terms "treatment" or "treating" relate to any treatment of acute heart failure, as well as to prevent or delay disease onset. Such treatments include, for example, ameliorating or relieving the symptoms associated with acute heart failure, as well as targeting underlying causes. As will be understood by those of ordinary skill in the art, when the term "prevent" or "prevention" is used in connection with a prophylactic treatment, it should not be understood as an absolute term that would preclude any sign of acute heart failure in a subject. Rather, as used in the context of prophylactic treatment, the term "prevent" can refer to reducing the likelihood of acute heart failure, heart failure, and/or symptoms associated therewith, such as in a subject who may be at high risk for acute heart failure. Those of ordinary skill in the art will be familiar with treatment for acute heart failure, and additional information about treatment can be found in the cited references, the disclosures of which are incorporated by reference.[23,37,38]

As used herein, the term "subject" refers to an animal, including a mammal, such as a human being.

Exemplary Embodiments

Exemplary methods disclosed herein involve detecting angiopoietin-2 (Angpt-2) and/or thrombospondin-2. In some embodiments, the method involves obtaining or having obtained a blood or plasma sample from the subject; and detecting or having detected Angpt-2 and Tsp-2 in the sample. Detecting can involve performing or having performed an assay to determine whether the sample includes Angpt-2 and/or Tsp-2 or elevated levels of Angpt-2 and/or Tsp-2.

In some embodiment, the method also includes diagnosing the subject with acute heart failure when there is an elevated presence of Angpt-2 and/or Tsp-2 in the sample. In some embodiments, the method also includes administering treatment for acute heart failure to the subject when there is an elevated presence of Angpt-2 and/or Tsp-2 in the sample.

In some embodiment, the method also includes identifying the subject as having an increased risk of developing heart failure. In some embodiments, the method also includes administering treatment to the subject to prevent or delay disease onset when there is an elevated presence of Angpt-2 and/or Tsp-2 in the sample.

In some embodiments, the method also includes detecting or having detected natriuretic peptides in the sample. In some embodiments, the natriuretic peptides include one or more of B-type natriuretic peptide (BNP), N-terminal pro-BNP (NTproBNP), and mid-regional proatrial natriuretic peptide (MRproANP). In some embodiments, the method also involves administering treatment to the subject when there is an elevated presence of Angpt-2 and/or Tsp-2, and the natriuretic peptide levels are above a threshold level for excluding acute heart failure (e.g., >100 pg/ml).

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, in some embodiments ±0.001%, and in some embodiments ±0.0001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples are prophetic, notwithstanding the numerical values, results and/or data referred to and contained in the examples. The following examples may include compilations of data that are representative of data gathered at various times during the course of development and experimentation related to the present invention.

EXAMPLES

As disclosed herein, using electronic health records (EHRs) with discarded clinical specimens, patients with and without heart failure (HF) were identified and their discarded plasma was retrieved from the clinical laboratory. These specimens were screened using a DNA aptamer-based proteomic platform (1,129 proteins). Candidate biomarkers were subsequently validated in three different prospective cohorts: an emergency department based registry of dyspneic patients (STRATIFY, n=852), a community-based epidemiologic cohort (Malmo Diet and Cancer Study [MDCS], n=768), and a clinical study of patients before and after heart transplantation (n=30).

In an automated manner, plasma samples from 1,315 patients (31% with HF) were collected (~12 samples per day). Proteomic analysis of a random 96-person subset identified nine candidate HF biomarkers ($p<4.42\times10^{-5}$ for each). Two of these proteins, angiopoietin-2 and thrombospondin-2, were associated with HF in all three validation cohorts. In STRATIFY, measurement of angiopoietin-2 and thrombospondin-2 led to a higher area under the ROC curve for HF (C-statistic 0.78 [95% CI, 0.75 to 0.82]), compared with a clinical score alone (0.71 [0.68 to 0.75], p <0.0001) or a clinical score plus B-type natriuretic peptide (0.77 [0.73 to 0.80], p=0.02). In the MDCS, both biomarkers predicted incident HF independent of traditional risk factors and NTproBNP (hazard ratio per standard deviation increase for angiopoietin-2:1.35 [95% CI, 1.14 to 1.61, p=0.0007] and for thrombospondin-2:1.37 [1.06 to 1.79, p=0.02]).

Following cardiac transplantation, concentrations of both biomarkers declined:angiopoietin-2 (−84% [95% CI, −89 to −77]) and thrombospondin-2 (−80% [−87 to −70]), p <0.001 for both.

Methods

Discovery sample.

Procedures for Plasma Collection. Collection of plasma follows similar procedures in place for DNA collection for BioVU.[14,16] Blood specimens collected as part of routine clinical care are stored at 4° C. until they are picked up by designated technicians 3-5 days post draw date. Blood specimens collected in EDTA-treated tubes are collected daily from the Pathology Department refrigerator and taken to the Vanderbilt Technologies for Advanced Genomics (VANTAGE) Core, where they are immediately processed. Sample barcodes are scanned to select those matching BioVU criteria and sorted based upon eligibility for DNA, as well as plasma collection. Samples eligible for the plasma biobanking are centrifuged at 1,499×g for 15 min, and only samples with a minimum plasma volume of 500 microliters are retained. Plasma fractions are transferred and stored at −80° C. until collected by the investigative team.

Figure 1:
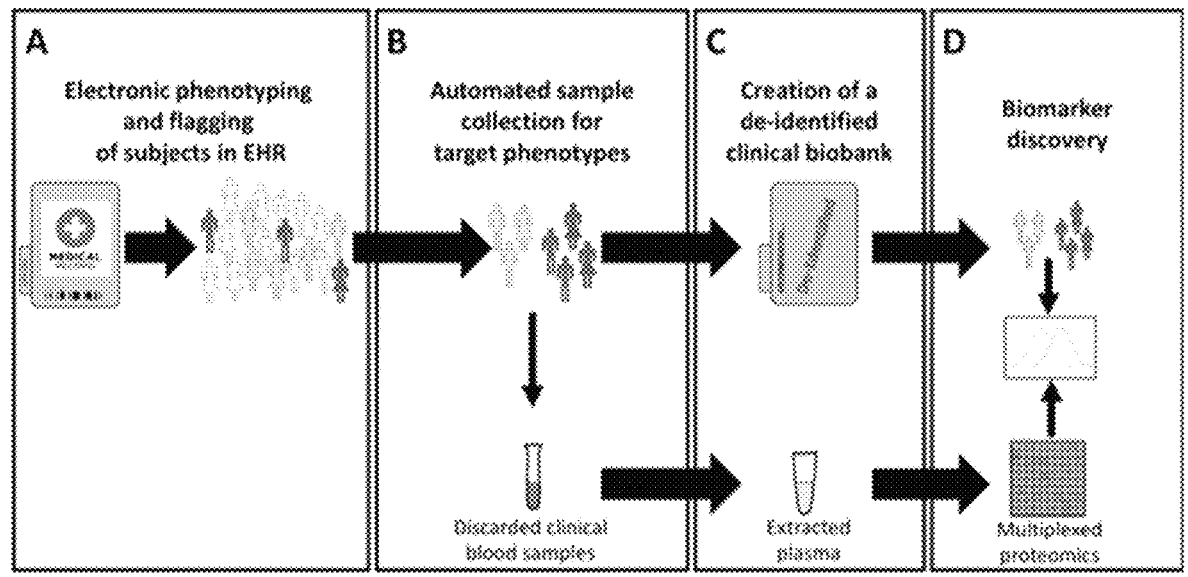
FIG. 1. Schematic of automated plasma collection and proteomic analysis procedures. Panel A: Electronic algorithms are deployed in an electronic health record (EHR) database for real-time identification of subjects with and without heart failure. Panel B: Discarded clinical blood samples from eligible subjects are flagged for automated collection, plasma extraction, and sample storage. Panel C: Plasma samples are linked with de-identified EHRs and incorporated into a de-identified biobank. Panel D: Discovery of novel candidate heart failure biomarkers by analysis of plasma from cases and controls using a DNA aptamer-based proteomic platform.

The discovery cohort was developed using a de-identified version of the Vanderbilt University Medical Center (VUMC) EHR. The EHR is linked to BioVU, the VUMC biorepository that houses DNA extracted from residual blood samples collected during routine clinical care that would otherwise be discarded.[14,15] For the current project, BioVU was adapted to include collection of residual clinical plasma (FIG. 1).[16]

Electronic Health Record Clinical Phenotype: Algorithm Definitions

Bioinformatic algorithms were developed to identify both ambulatory and hospitalized patients from 3 groups: 1) patients with prevalent HF; 2) patients with cardiovascular disease but without HF; and 3) patients with neither cardiovascular disease nor HF.

The algorithms were iteratively refined through manual review of EHRs (N=50 per iteration) and validated by cardiologist review of an independent sample of EHRs (N=100 per phenotype).

Group 1: Subjects with heart failure
Include: Age≥40 AND 2 or more ICD-9 codes (either of the following): 425.* or 428.* AND Labs (at least one value present): BNP>500 pg/ml AND Medications (one or more, any of the following, using generic or brand names): Furosemide, Bumetanide, Torsemide, Ethacrynic Acid Group 2: Subjects without heart failure
Include: Age≥40

Exclude: 1 or more ICD-9 codes: 425.* or 428.* AND Labs: BNP>100 pg/ml AND Medications (one or more, any of the following, using generic or brand names): Furosemide, Bumetanide, Torsemide, Ethacrynic Acid Group 3: Subjects without heart failure and no cardiovascular disease
Include: All criteria for Group 2
Exclude: 1 or more ICD-9 codes (any of the following): 250.*, 403.*, 404.*, 414.*, 430.*, 431.*, 432.*, 433*-435.*, 440.*, 491.*, 492.*, 496.*, 585.*, 272.*, 427.* OR CPT code (any of the following): 33510-33523, 33533, 33536, 92980, 92984, 92995, 92996, 47135, 47136, 50360, 50365, 32851, 32852, 32854 OR Labs (any of the following): Hemoglobin A1 c >6.0%, Glucose≥200 mg/dL, Serum creatinine≥1.5 mg/dL.

Figure 7:
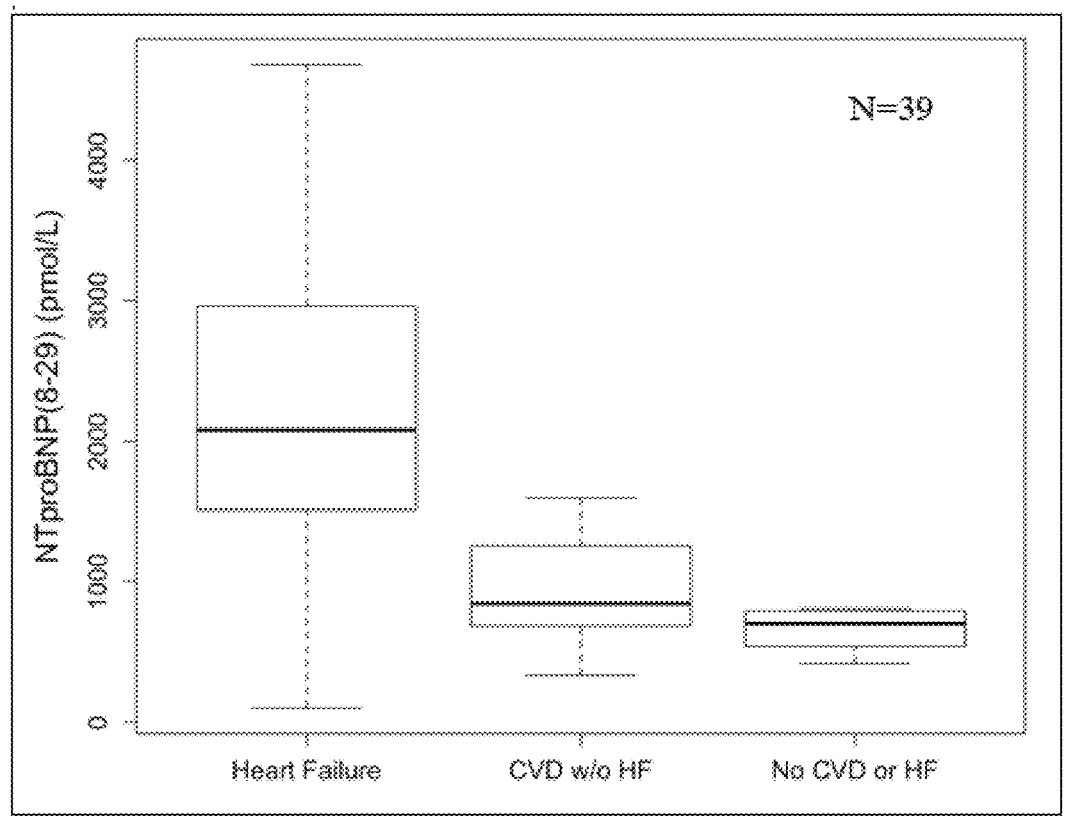
FIG. 7. Plasma NTproBNP levels from a subset of bioinformatically identified phenotypes. NTproNP levels significantly differed (p=0.012) according to heart failure and cardiovascular disease status among a subset of patients identified using the automated electronic health record algorithm (group 1, HF: 2,078 pmol/L [1,512-2,958]; group 2, cardiovascular disease without HF: 843 pmol/L [684-1,259]; group 3, no HF or cardiovascular disease: 701 pmol/L [538-788]. The assay used detects NTproBNP 8-29 (BNP Fragment EIA, Catalog #BI-20852W, Alpco, Salem, N. H.) at a lower detection limit of 171 pmol/L.

The positive predictive value for all algorithms was ≥95%, and N-terminal pro B-type natriuretic peptide (NT-proBNP) levels also rose in the expected manner across a random sample of subjects from each clinical group (FIG. 7).

Algorithms were deployed for 110 days between September 2014 and September 2015 for real-time identification of patients. Subjects meeting one of the three phenotype definitions were flagged in the computer system, and then, in the clinical pathology laboratory, their residual blood samples were retrieved after the clinically-indicated storage period of three days at 4° C. The samples were robotically processed for plasma extraction and stored at −80° C. From all collected samples, a random subset of 96 was selected, in a 1:1 ratio from groups one (HF) and three (no HF or cardiovascular disease), for proteomic analysis. The Vanderbilt Institutional Review Board approved this study and all subjects consented to participate in BioVU.

Validation samples.

Candidate biomarkers were first tested for validation in the Improving Heart Failure Risk Stratification in the ED study (STRATIFY), a multi-center, prospective, observational cohort of 2,004 patients (≥18 years old) with dyspnea and suspected acute HF from four EDs in Nashville, Tenn. and Cincinnati, Ohio between 2007 to 2011 (NCT00508638).[7] Within three hours of ED presentation, trained research staff collected a standardized set of demographic, clinical, and laboratory variables, and in a subset of patients, blood samples were also collected, immediately processed for plasma, and stored frozen at −80° C. Management decisions were made by treating ED physicians and not STRATIFY investigators. The presence of acute HF was determined by an adjudication committee of three board-certified cardiologists with access to clinical data from the entire hospitalization (ED encounter plus inpatient stay). A total of 852 STRATIFY patients had plasma samples available for this analysis. The characteristics of studied patients did not substantially differ from patients excluded due to lack of an available plasma sample (Table 1). The institutional review boards of each of the four EDs approved the STRATIFY study and all patients provided written informed consent.

TABLE 1

Baseline characteristics of STRATIFY patients according to whether they were included or excluded from the biomarker plasma study.

|  | Excluded N = 1152 | Included N = 852 | p |
|---|---|---|---|
| Age, years | 60 (51,72) | 63 (53, 75) | 0.001 |
| Female, % | 46 | 45 | 0.68 |

TABLE 1-continued

Baseline characteristics of STRATIFY patients according to whether they were included or excluded from the biomarker plasma study.

|  | Excluded N = 1152 | Included N = 852 | p |
|---|---|---|---|
| Black, % | 49 | 34 | <0.001 |
| Exertional dyspnea | 91 | 90 | 0.45 |
| Nocturnal cough | 46 | 47 | 0.72 |
| Orthopnea | 70 | 70 | 0.80 |
| Paroxysmal nocturnal dyspnea | 43 | 44 | 0.65 |
| Hx of Heart Failure, % | 69 | 66 | 0.21 |
| Hx of CAD, % | 48 | 46 | 0.29 |
| Hx of Valvular HD, % | 18 | 24 | 0.004 |
| Hx of Hypertension, % | 83 | 80 | 0.069 |
| Hx of diabetes | 44 | 42 | 0.49 |
| Hx of renal disease, % | 21 | 23 | 0.70 |
| Hx of COPD, % | 31 | 33 | 0.50 |
| Aspirin, % | 50 | 50 | 0.15 |
| ACEI or ARB, % | 54 | 52 | 0.26 |
| Beta-blocker, % | 63 | 60 | 0.03 |
| Diuretic, % | 64 | 66 | 0.14 |
| BMI, kg/m$^2$ | 31 (26, 38) | 30 (26, 37) | 0.31 |
| Systolic BP, mmHg | 141 (124, 166) | 142 (125, 163) | 0.57 |
| Diastolic BP, mmHg | 81 (69, 97) | 80 (69, 93) | 0.31 |
| Heart Rate, bpm | 88 (76, 102) | 86 (73, 100) | 0.036 |
| JVD present | 16 | 19 | 0.036 |
| Rales | 50 | 53 | 0.18 |
| S3 gallop | 7 | 9 | 0.36 |
| Hepatomegaly | 3 | 3 | 0.60 |
| Hepatojugular reflux | 6 | 6 | 0.64 |
| Lower extremity edema | 59 | 65 | 0.009 |
| eGFR, ml/min/1.73 m$^2$ | 57 (34, 81) | 54 (35, 80) | 0.68 |
| CXR cardiomegaly | 62 | 52 | <0.001 |
| CXR pulmonary edema | 42 | 41 | 0.58 |
| CXR pleural effusion | 23 | 23 | 0.96 |
| LVEF, % | 50 (30, 60) | 50 (35, 60) | 0.20 |
| BNP (local), pg/ml | 486 (119, 1150) | 498 (160, 1130) | 0.73 |
| Acute heart failure | 48 | 48 | 0.92 |

Values shown as median ($25^{th}$, $75^{th}$ percentile) or percentages. CAD = coronary artery disease; HD = heart disease; COPD = chronic obstructive pulmonary disease; ACEI = angiotensin converting enzyme inhibitor; ARB = angiotensin receptor blocker; BMI = body mass index; BP = blood pressure; JVD = jugular venous distension; eGFR = estimated glomerular filtration rate; CXR = chest x-ray; LVEF = left ventricular ejection fraction; BNP = B-type natriuretic peptide.

Biomarkers that validated in STRATIFY underwent testing in two additional cohorts. First, the Malmo Diet and Cancer Study (MDCS) was used, which is a population-based, prospective cohort of 30,447 individuals from Malmö, Sweden. The MDCS allows assessment of the biomarkers' ability to predict future HF among individuals without a prior history of the disease. Participants were enrolled between 1991 and 1996, with follow up through Dec. 31, 2013. From the overall MDCS, 185 individuals with incident HF and plasma available, and 583 randomly sampled cohort-representative non-HF controls with plasma available were selected for analysis of the candidate biomarkers.[18] Incident HF was ascertained from the Swedish Hospital Discharge Register using primary position diagnosis codes 427.00, 427.10, and 428.99 for International Classification of Diseases 8th Revision (ICD-8), 428 for the 9th Revision (ICD-9), and ISO and 111.0 for the 10th Revision (ICD-10), which have previously been demonstrated through manual adjudication to have high validity (positive predictive value 95%)[19]

Second, the biomarkers were measured in patients with established HF undergoing heart transplantation or left ventricular assist device (LVAD) implantation. Advanced HF patients were recruited from Skane University Hospital in Lund, Sweden, between 2012 and 2016.

Plasma samples were collected at the time of right heart catheterization as part of routine clinical assessment to determine heart transplant eligibility. Samples were collected from a total of 30 patients prior (median 99 days [range 4-983]) to and at the six-month follow-up after (median 167 days [range 149-219]) heart transplantation. Samples were also collected from six patients prior to and following LVAD placement, with a median number of days between sample acquisition and LVAD of 61 (range 5 to 127) and 60 (40 to 834), respectively. All LVAD patients, except one, subsequently underwent heart transplantation and were included in both cohorts. Samples were immediately processed for plasma, stored at −80° C., and only thawed at the time of biochemical analysis for the current study. The Ethics Committee of Lund University, Sweden, approved both the MDCS and the advanced HF study, and all participants provided informed consent.

The Malmö Diet and Cancer Study: Brief Description. The Malmö Diet and Cancer Study (MDCS) is a prospective cohort study which includes 30,447 men (born between 1923-1945) and women (born between 1923-1950) from the city of Malmo in southern Sweden who underwent baseline examinations between 1991 and 1996. From this cohort 6,103 individuals with a baseline examination between 1991 and 1994 were randomly selected to participate in a study of cardiovascular risk factors, the MDCS Cardiovascular Cohort (MDC-CC), of whom 5,543 underwent blood sampling under standardized fasting conditions.[35,36] Blood pressure (systolic and diastolic) was measured using a mercury-column sphygmomanometer after 10 minutes of rest in the supine position. Data on current smoking, diabetes mellitus and use of antihypertensive and antidiabetic medications was ascertained from a questionnaire. Diabetes mellitus was defined as fasting blood glucose >6.0 mmol/L, self-reported physician diagnosis or use of antidiabetic medications. MDCS was approved by the Ethics Committee of Lund University, Sweden, and all individuals provided informed consent.

Advanced Heart Failure Cohort. Peripheral venous plasma samples were drawn serially from patients with advanced heart failure undergoing right heart catheterization between 2012 and 2016 as part of the routine assessment of eligibility for transplant or left ventricular assist device (LVAD) at the Department of Heart Failure and Valvular Disease of Skane University Hospital in Lund, Sweden. Skane University Hospital is one of two heart transplant centers in Sweden, serving roughly half of the Swedish population with an average surgical volume of 30 heart transplants per year. Only subjects living in the secondary care catchment area of Skane University Hospital and scheduled for follow-up at this institution were considered for study inclusion. Samples were obtained before surgery and from the same patients at the time of the 6-month follow-up right heart catheterization with biopsy after heart transplantation (n=30) or at follow-up catheterization after placement of a LVAD (n=6). Baseline samples were collected at a median of 99 days before transplantation (range 4-983) or 61 days before LVAD placement (range 5-127). Follow-up samples were collected at a median of 167 days after heart transplantation (range 149-219) or 60 days after LVAD placement (range 40-834). All LVAD patients except one subsequently underwent heart transplantation and were included in both cohorts. Samples were immediately processed for plasma, stored at −80° C. and only thawed at the time of biochemical analysis for the current study. The study was approved by the local ethics committee of Lund University and all participants provided informed consent.

Laboratory methods.

Biomarker measurements in the discovery sample, MDCS, and transplant/LVAD patients were performed using the SOMAscan platform (SOMALogic Inc., Boulder, Colo.).[20, 21] This technology uses single-stranded DNA aptamers that target 1,129 proteins with antibody-like specificity (full list in reference).[22]

Figure 6:
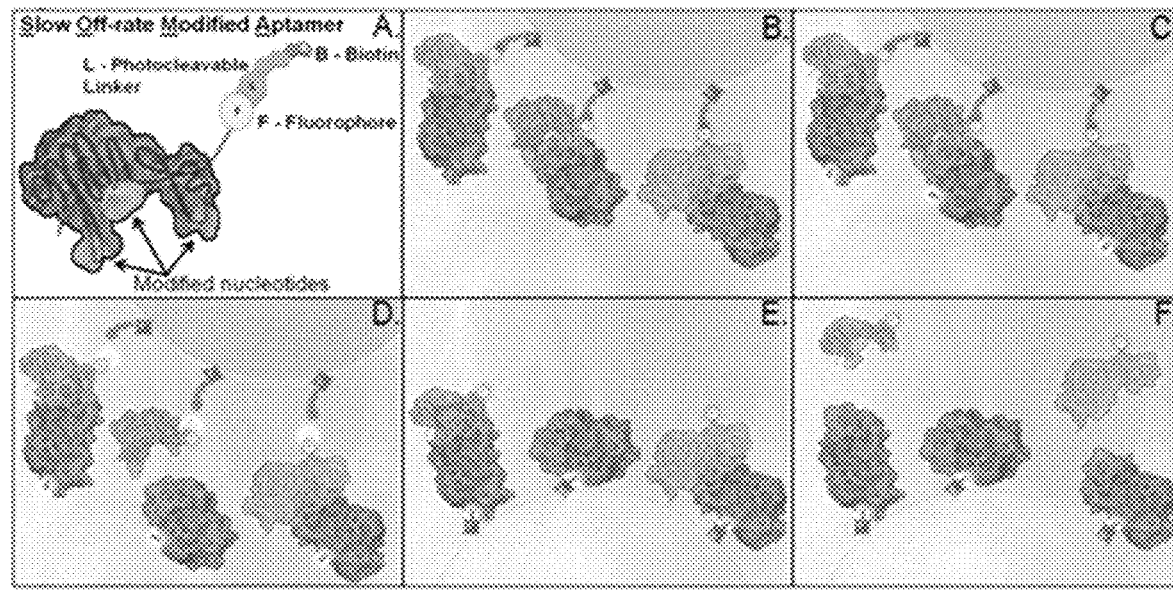
FIG. 6. Illustration of proteomic analysis using SOMAscan DNA-aptamer array. A SOMAmer reagent is a single-stranded DNA-based aptamer chemically modified to augment high affinity and specificity binding to conformational protein epitopes. The reagent's flourophore tag allows detection by standard oligo-array readers (FIG. 6, Panel A demonstrates details of SOMAmer® structure). A multi-step capture, release, and re-capture enrichment process allows the assay to measure proteins directly from plasma. Plasma proteins (purple) first bind to bead-immobilized SOMAmers® (FIG. 6, Panel B). The SOMAmer®-bound proteins are then biotinylated (FIG. 6, Panel C). Next, a photocleavage process releases SOMAmer®-protein complexes and non-specific pairs are disrupted (FIG. 6, Panel D). Subsequently, biotinylated proteins are bound to a second streptavidin bead (FIG. 6, Panel E). Following a washing step, SOMAmers® released from the protein targets are collected (FIG. 6, Panel F). The fluorophore-tagged modified nucleotides are then quantitated on an oligo-array plate reader (Agilent Technologies).

Proteomic analysis using SOMAscan DNA-aptamer array (SOMALogic Inc., Boulder, Colo.)[21] is described, with reference to FIG. 6. Correction for systematic effects on data introduced during hybridization was done by 12 hybridization control sequences introduced into each clinical sample. A predetermined global reference relative fluorescence unit (RFU) for each hybridization control was based on independently run assays. A ratio is determined by this global RFU for each control/measured RFU of each hybridizaton control. The median of the ratios determines the sample based hybridization scale factor, with each sample multiplied by its own scale factor.

To remove sample or assay biases (that may be due to differences between samples in overall protein concentration, pipetting variation, variation in reagent concentrations, assay timing, and any other source of systematic variability within a single plate run) median normalization was performed. Each sample was diluted either to 40%, 1% or 0.05%. A scale factor was derived for each dilution set and all the SOMAmers in each dilution set are scaled together. Median RFU for a SOMAmer within the sample group was the reference SOMAmer RFU. A ratio was determined by the reference SOMAmer RFU/measured RFU of the SOMAmer in the sample. Within each dilution set, the median SOMAmer ratio was the scale factor for all SOMAmers in that dilution in that sample. Based on historic trends, the acceptance criteria for these values are 0.4 to 2.5.

The global reference RFU for each SOMAmer was defined as the median signal measured on a set of samples spanning a number of independent assay runs. A total of 5 calibrator samples, which comprise of human pooled plasma, were on each plate. A local median reference value was derived for each SOMAmer by computing the median RFU for that SOMAmer from the within plate 5 calibrator samples. The ratio of the global reference calibrator for the SOMAmer/local median reference value of the SOMAmer determined the scale factor; each SOMAmer on each plate has a unique scale factor. The acceptance criterion for calibrator scale factors is that 95% of SOMAmers must have a calibration scale factor within 60.4 of the median. Calibrator samples were also used to calculate intra-assay coefficient of variation.

In addition, plasma from one individual was run as 2 quality control (QC) samples on each plate, with QC samples normalized as above. Hybridization normalized, median normalized and calibrated QC samples were then used to calculate inter-assay coefficients of variation for each SOMAmer because calibration by definition will minimize the plate-to-plate variance of the calibrator samples.

In STRATIFY, biomarkers were measured using commercially-available enzyme-linked immunosorbent assays (Table 2). B-type natriuretic peptide (BNP) was measured locally at each ED, using assays in which values <100 pg/ml were considered not suggestive of acute HF. In the MDCS, NTproBNP was measured using the automated Dimension Vista Intelligent Lab System method (Siemens Healthcare Diagnostics Inc., Deerfield, Ill.) as previously described.[18] In the advanced HF cohort, NTproBNP was measured using an electrochemiluminiscence sandwich immunoassay in the fully automated Elecsys E170 analyzer (Roche Diagnostics, Indianapolis, Ind.). All laboratory personnel were blinded to clinical data.

TABLE 2

Characteristics of human enzyme linked immunosorbent assays for candidate circulating biomarkers.

| Protein | Units | Manufacturer | Assay Detail | Detection limits/Sensitivity |
|---|---|---|---|---|
| Angiopoietin-2 | pg/mL | Invitrogen Corporation, 7335 Executive Way, Frederick, MD, 21704 | ELISA Kit Invitrogen, Catalog #KHC1641 | <6 pg/mL |
| Thrombospondin-2 | ng/mL | R&D Systems, 614 McKinley Place NE, Minneapolis, MN 55413 | Quantikine ELISA Kit Catalog# DTSP20 | 0.068 ng/mL |

TABLE 2-continued

Characteristics of human enzyme linked immunosorbent assays for candidate circulating biomarkers.

| Protein | Units | Manufacturer | Assay Detail | Detection limits/Sensitivity |
|---|---|---|---|---|
| Interleukin 17 Receptor C | ng/mL | RayBiotech, 3607 Parkway Lane, Suite 100, Norcross, GA 30092 | RayBio Human IL-17RC ELISA Kit, Catalog #ELH-IL17RC | 0.05 ng/mL |
| Insulin like growth factor binding protein-6 | pg/mL | Invitrogen Corporation, 7335 Executive Way, Frederick, MD 21704 | Human IGFBP-6 ELISA Kit, Catalog# EHIGFBP6 | 150 pg/mL |

Statistical Analysis.

In the discovery sample, proteins were considered for validation if all of the following criteria were met: 1) significant difference between HF cases and non-HF controls (Wilcoxon rank-sum test) using a Bonferroni-corrected p-value threshold ($4.42 \times 10^{-5} = 0.05/1,129$ proteins), 2) median concentrations for cases and controls differed by >50%, and 3) associated with HF in a multivariable logistic regression model adjusted for age, sex, blood pressure, and estimated glomerular filtration rate (eGFR).

In STRATIFY, biomarkers were tested for association with acute HF in unadjusted (Wilcoxon rank-sum test) and multivariable-adjusted logistic regression analyses. Covariates were age, sex, race, clinical HF criteria (Framingham), prior history of HF, BMI, eGFR, and BNP. Diagnostic performance was assessed using receiver operating characteristic curve (ROC) analyses with Sidak's correction for multiple testing. The ROC analyses compared the diagnostic performance of 1) a clinical HF score (Framingham major criteria=two points, minor criteria=one point) alone, 2) clinical HF score plus BNP, and 3) clinical HF score plus BNP and each of the biomarkers. Analyses were also performed to identify cut-point values for each of the candidate biomarkers that maximized the sum of sensitivity and specificity (Youden's statistic) for the diagnosis of acute HF, and to compare the diagnostic performance of the new biomarkers at their cut-points with the currently accepted clinical threshold of 100 pg/ml of BNP (Sidak corrected). Logistic regression was also used to calculate predicted probabilities for acute HF for the candidate biomarkers on a continuous scale among patients with BNP>100 pg/ml.

In the MDCS, the association between biomarkers and risk of incident HF was assessed using Prentice-weighted Cox proportional hazards models with robust variance estimators. Biomarkers were natural log-transformed and standardized. Covariates in the multivariable-adjusted models included age, sex, systolic blood pressure, diastolic blood pressure, antihypertensive drug use, prevalent diabetes, BMI, low density lipoprotein (LDL) cholesterol, high density lipoprotein (HDL) cholesterol, current smoking, prevalent myocardial infarction, and NTproBNP. The proportionality of hazards assumption was confirmed using Schoenfeld's global test. Discrimination for each model was examined using Harrell's C-statistics. Cumulative HF incidence across biomarker tertiles was obtained from nonparametric estimates of the cumulative incidence function.

In the transplantation and LVAD samples, the change in biomarker levels before and after transplant or LVAD was visualized using box plots and assessed using the Wilcoxon signed-rank test and linear mixed models.

All analyses were performed with R 3.1.3 (R Foundation for Statistical Computing, Vienna, Austria) or Stata v12.1 or 13.0 (Stata Corp. LLC, College Station, Tex.). DKG, QSW, and JGS had access to all of the data in the study and all authors had final responsibility for the decision to submit for publication.

Results

Automated Biobanking and Biomarker Discovery

During the automated collection phase, 1,315 discarded plasma samples were collected (group one, HF: n=412; group two, cardiovascular disease without HF: n=571; group three, no HF or cardiovascular disease: n=332), at a mean rate of 12 samples per day. The median age of patients was 64 years, and 52% of patients were female. The majority of patients were white (86%). Full characteristics of the sample are shown in Table 3.

TABLE 3

Characteristics of the 1,315 subjects in the BioVU plasma biobank

| | Overall N = 1,315 (100) | Group 1 HF N = 412 (31) | Group 2 No HF N = 571 (43) | Group 3 No CVD or HF N = 332 (25) |
|---|---|---|---|---|
| Age, years | 64 (54, 73) | 68 (60, 76) | 65 (57, 73) | 54 (48, 65) |
| Male | 625 (48) | 249 (60) | 290 (51) | 86 (26) |
| Race | | | | |
| White | 1,129 (86) | 345 (84) | 488 (86) | 296 (89) |
| Black | 148 (11) | 59 (14) | 67 (12) | 22 (7) |
| Other | 38 (3) | 8 (2) | 16 (2) | 14 (4) |
| Diabetes | 300 (23) | 149 (36) | 147 (26) | 4 (1) |
| CAD | 580 (44) | 361 (88) | 215 (38) | 0 (0) |
| Hypertension | 1,023 (78) | 401 (97) | 481 (84) | 141 (43) |
| BMI, kg/m² | 28 (25, 32) | 28 (25, 32) | 28 (25, 32) | 27 (23, 31) |
| Systolic BP, mmHg | 124 (116, 133) | 120 (109, 130) | 128 (121, 135) | 123 (115, 131) |
| Diastolic BP, mmHg | 70 (64, 76) | 65 (60, 70) | 71 (66, 77) | 73 (69, 79) |
| eGFR, ml/min/1.73 m² | 73 (52, 91) | 51 (35, 69) | 75 (58, 93) | 86 (75, 97) |
| LVEF, % | 55 (45, 60) | 52 (32, 55) | 55 (55, 60) | 55 (55, 60) |

Values presented as n (%) or median ($25^{th}$, $75^{th}$ percentile). HF = heart failure, CVD = cardiovascular disease, BMI = body mass index, BP = blood pressure, eGFR = estimated glomerular filtration rate, LVEF = left ventricular ejection fraction, CAD = coronary artery disease.

The proteomic assay was successfully completed in 95 of 96 samples (99%) in the random patient subset. Compared with those free of HF, individuals with HF were older (median 66 vs. 59 years, p=0.03), more commonly male (56 vs. 23%, p=0.002), and had a higher burden of comorbidities such as hypertension, diabetes, and coronary artery disease (Table 4). Of the 1,129 proteins assayed, nine (0.8%) met selection criteria as candidate biomarkers (Table 2). Because the top two proteins (cystatin C and renin) had known associations with HF, the next four proteins (thrombospondin-2, insulin like growth factor binding protein-6, angiopoietin-2, and interleukin-17 receptor C) were selected for validation.

TABLE 4

Characteristics of BioVU patients with and without heart failure in whom the proteomic analysis was successfully completed.

|  | HF N = 48 | No HF or CVD N = 47 | $p^a$ |
|---|---|---|---|
| Age, years | 66 (61, 74) | 59 (49, 69) | 0.034 |
| Male, % | 56 | 23 | 0.002 |
| Black, % | 13 | 11 | >0.99 |
| BMI, kg/m² | 27.8 (24.0, 32.5) | 27.0 (23.0, 31.2) | 0.16 |
| Systolic BP, mmHg | 123 (110, 130) | 124 (114, 131) | 0.27 |
| Diastolic BP, mmHg | 65 (61, 70) | 72 (69, 78) | <0.001 |
| eGFR, ml/min/1.73 m² | 52 (36, 77) | 83 (73, 96) | <0.001 |
| LVEF, % | 55 (34, 56) | 55 (55, 60) | 0.07 |
| Diabetes, % | 35 | 0 | <0.001 |
| Hypertension, % | 98 | 40 | <0.001 |
| CAD, % | 92 | 0 | <0.001 |

Values presented as median ($25^{th}$, $75^{th}$ percentile). $^a$Wilcoxon rank sum or Fisher's Exact; BMI = body mass index, BP = blood pressure, eGFR = estimated glomerular filtration rate, LVEF = left ventricular ejection fraction, CAD = coronary artery disease.

TABLE 5

Candidate heart failure biomarkers based upon DNA-aptamer proteomic results from discarded clinical plasma specimens

| | Relative Florescence Units | | | |
|---|---|---|---|---|
| Protein | HF | No HF | p | % Difference |
| Cystatin-C | 2272 (1896, 2963) | 1434 (1263, 1772) | $2.04 \times 10^{-10}$ | 58 |
| Renin | 1238 (709, 1945) | 393 (289, 610) | $4.74 \times 10^{-10}$ | 215 |
| Thrombospondin-2 | 21260 (13500, 32150) | 9094 (7242, 13680) | $9.60 \times 10^{-9}$ | 134 |
| Insulin like growth factor binding protein-6 | 697 (516, 884) | 442 (406, 514) | $1.46 \times 10^{-8}$ | 58 |
| Angiopoietin-2 | 593 (461, 791) | 393 (331, 468) | $3.51 \times 10^{-7}$ | 51 |
| Interleukin-17 receptor C | 1729 (1331, 2329) | 1065 (882, 1389) | $4.24 \times 10^{-7}$ | 62 |
| Kallikrein-11 | 1866 (1206, 2279) | 1073 (901, 1339) | $4.58 \times 10^{-7}$ | 74 |
| Macrophage colony-stimulating factor-1 | 2166 (1663, 2733) | 1292 (1138, 1553) | $6.87 \times 10^{-7}$ | 68 |
| Leukotriene A-4 hydrolase | 1763 (1165, 2344) | 955 (796, 1187) | $4.60 \times 10^{-6}$ | 85 |

Values presented at median ($25^{th}$, $75^{th}$ percentile). HF = heart failure.

Biomarker Validation in Acute HF Samples

Figure 2:
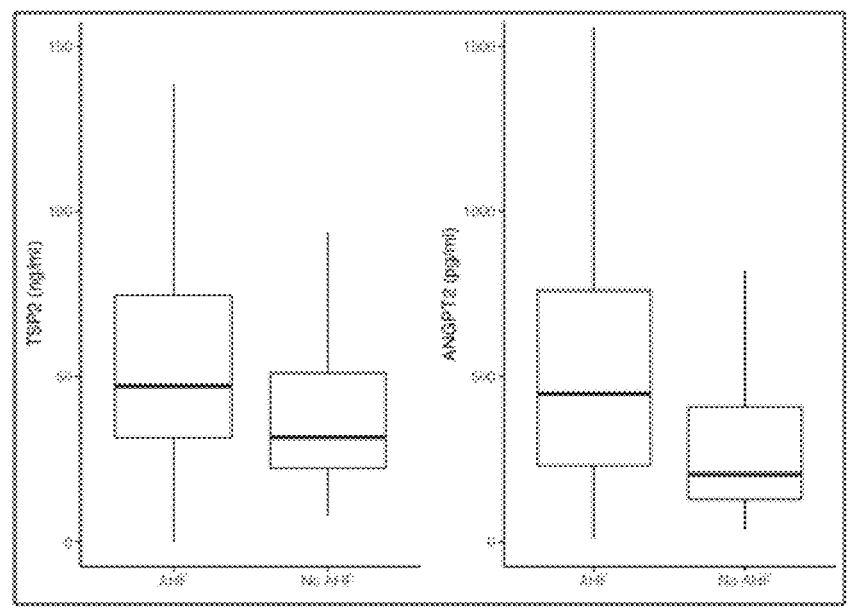
FIG. 2. Circulating thrombospondin-2 and angiopoietin-2 levels in patients with and without acute heart failure presenting to the emergency department. Box plots of circulating thrombospondin-2 (Tsp-2) and angiopoietin-2 (Angpt-2) levels in the emergency department based validation cohort (STRATIFY), $p<0.001$ for both. AHF=acute heart failure.

In STRATIFY, 405 of 852 patients (48%) had cardiologist-adjudicated acute HF. Individuals with acute HF were older, had more dyspnea, more commonly had a prior history of HF, and more frequently had physical exam signs and chest x-ray findings suggestive of acute HF (Table 6). Concentrations of thrombospondin-2 and angiopoietin-2, but not the other candidate biomarkers, were significantly higher in patients with acute HF (p<0.001 for both, FIG. 2).

TABLE 6

Characteristics of patients presenting to the emergency department in the STRATIFY plasma study cohort according to adjudicated acute heart failure status.

|  | Not Acute Heart Failure N = 447 (52%) | Acute Heart Failure N = 405 (48%) | p |
|---|---|---|---|
| Age, years | 62 (52, 74) | 65 (55, 76) | 0.016 |
| Female, % | 47 | 44 | 0.45 |
| Black, % | 32 | 35 | 0.43 |
| Exertional dyspnea | 86 | 94 | <0.001 |

TABLE 6-continued

Characteristics of patients presenting to the emergency department in the STRATIFY plasma study cohort according to adjudicated acute heart failure status.

|  | Not Acute Heart Failure N = 447 (52%) | Acute Heart Failure N = 405 (48%) | p |
|---|---|---|---|
| Nocturnal cough | 48 | 49 | 0.24 |
| Orthopnea | 67 | 73 | 0.043 |
| Paroxysmal nocturnal dyspnea | 38 | 52 | <0.001 |
| Hx of Heart Failure, % | 59 | 75 | <0.001 |
| Hx of Coronary Artery Disease, % | 44 | 48 | 0.37 |
| Hx of Valvular Heart Disease, % | 19 | 30 | <0.001 |
| Hx of Hypertension, % | 81 | 79 | 0.16 |
| Hx of Diabetes | 40 | 44 | 0.33 |
| Hx of Renal disease, % | 20 | 26 | 0.13 |
| Hx of COPD, % | 42 | 23 | <0.001 |
| Aspirin, % | 52 | 48 | 0.23 |
| ACEI or ARB, % | 47 | 57 | 0.007 |
| Beta-blocker, % | 55 | 65 | 0.001 |
| Diuretic, % | 60 | 73 | <0.001 |
| Body mass index, kg/m$^2$ | 31 (25, 38) | 30 (26, 37) | 0.66 |
| Systolic BP, mmHg | 141 (126, 159) | 143 (125, 168) | 0.23 |
| Diastolic BP, mmHg | 80 (67, 92) | 81 (70, 96) | 0.034 |
| Heart Rate, bpm | 86 (73, 98) | 86 (74, 100) | 0.49 |
| JVD present | 15 | 24 | 0.002 |
| Rales | 47 | 60 | <0.001 |
| S3 gallop | 5 | 12 | 0.001 |
| Hepatomegaly | 3 | 2 | 0.53 |
| Hepatojugular reflux | 4 | 9 | 0.017 |
| Lower extremity edema | 62 | 70 | 0.003 |
| eGFR, ml/min/1.73 m$^2$ | 59 (36, 86) | 52 (32, 75) | 0.007 |
| CXR cardiomegaly | 37 | 69 | 0.001 |
| CXR pulmonary edema | 28 | 55 | <0.001 |
| CXR pleural effusion | 17 | 28 | 0.004 |
| LVEF, % | 55 (45, 60) | 40 (25, 55) | <0.001 |
| BNP, pg/ml | 226 (64, 618) | 780 (417, 1509) | <0.001 |

Values shown are median (25$^{th}$, 75$^{th}$ percentile) or percentages. Hx = history; chronic obstructive pulmonary disease; ACEI = angiotensin converting enzyme inhibitor; ARB = angiotensin receptor blocker; BP = blood pressure; JVD = jugular venous distension; eGFR = estimated glomerular filtration rate; CXR = chest x-ray; LVEF = left ventricular ejection fraction; BNP = B-type natriuretic peptide.

In multivariable models adjusted for age, sex, race, Framingham HF criteria, prior HF, BMI, eGFR, and BNP, both angiopoietin-2 and thrombospondin-2 were associated with acute HF. The odds ratios per SD increase in biomarker were 1.36 (95% confidence interval, 1.09-1.69) for angiopoietin-2, and 1.50 (1.22-1.84) for thrombospondin-2 (Table 7).

TABLE 7

Multivariable-adjusted association between B-type natriuretic peptide, angiopoietin-2, and thrombospondin-2 and the diagnosis of acute heart failure among patients presenting to the emergency department.

| Variable | Odds ratio (95% Confidence Interval) | p |
|---|---|---|
| Age, per 1 year | 1.03 (1.01, 1.04) | <0.001 |
| Male | 0.98 (0.70, 1.36) | 0.90 |
| White | 0.91 (0.63, 1.31) | 0.60 |
| Framingham criteria for HF | 3.00 (1.75, 5.15) | <0.001 |
| History of HF | 2.24 (1.57, 3.19) | <0.001 |
| Body mass index (kg/m$^2$), per 1 unit | 1.03 (1.01, 1.04) | 0.009 |
| eGFR (ml/min/1.73 m$^2$), per 1 unit | 1.01 (1.00, 1.01) | 0.015 |
| B-type natriuretic peptide, per 1 SD | 1.88 (1.47, 2.42) | <0.001 |
| Angiopoietin-2, per 1 SD | 1.36 (1.09, 1.69) | 0.006 |
| Thrombospondin-2, per 1 SD | 1.50 (1.22, 1.84) | <0.001 |

HF = heart failure; eGFR = estimated glomerular filtration rate; SD = standard deviation. Standard deviations: B-type natriuretic peptide = 934 pg/ml; Angiopoietin-2 = 386 pg/ml; Thrombospondin-2 = 34 ng/ml.

Figure 3:
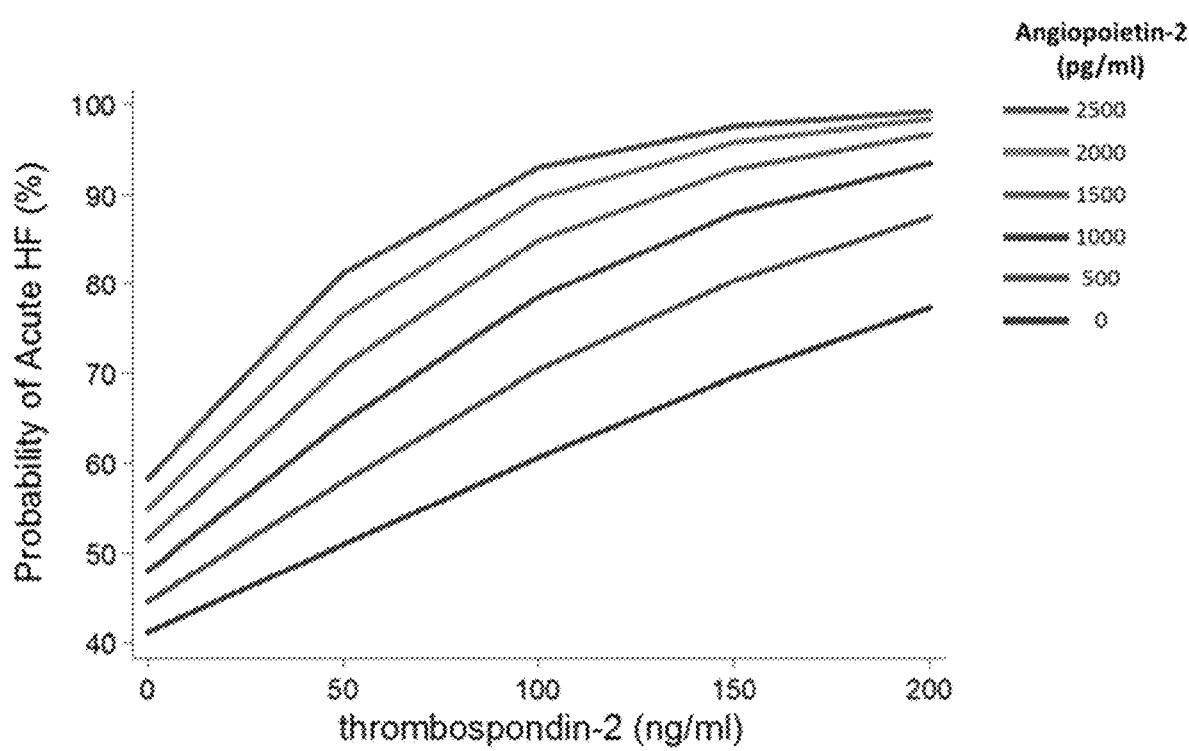
FIG. 3. Predicted probability of acute heart failure according to thrombospondin-2 and angiopoietin-2 levels among patients with suspected heart failure and B-type natriuretic peptide >100 pg/ml in the emergency department. Among patients presenting to the emergency department in whom the diagnosis of acute heart failure has not been excluded, i.e. B-type natriuretic peptide >100 pg/ml, additional knowledge of both thrombospondin-2 and angiopoietin-2 levels further stratifies the probability of acute heart failure across a broad range beyond either marker alone.

The potential diagnostic value of adding angiopoietin-2 and thrombospondin-2 to clinical variables and BNP was assessed in several ways. First, in ROC curve analyses, the addition of angiopoietin-2 and thrombospondin-2 levels to a clinical score and BNP significantly improved the C-statistic to 0.78 (95% CI, 0.75-0.82), compared with a clinical score alone (0.71 [0.68-0.75], p<0.0001) or clinical score plus BNP (0.77 [0.73-0.80], p=0.02). Second, among patients in whom acute HF had not been ruled-out (i.e., had BNP >100 pg/ml), levels of angiopoietin-2 and thrombospondin-2 provided additional stratification of HF risk across a wide range (probability of HF as high as 99% and as low as 40%) (FIG. 3). Third, angiopoietin-2 and thrombospondin-2 values that optimized sensitivity and specificity for differentiating acute HF from non-acute HF were identified as 228 pg/ml and 33 ng/ml, respectively. A simple score equal to the number of biomarkers (0-3, includes BNP) above their cut-points yielded a C-statistic of 0.73 (95% CI, 0.70-0.76), which was significantly better than that for BNP>100 pg/ml alone (0.65, 95% CI, 0.63-0.67; p<0.001) (Table 8). At a threshold of any one positive biomarker, the sensitivity of the score was 99% (95% CI, 97-100), though the specificity was only 24% (21-29). With three positive biomarkers, the specificity increased to 76% (72-80), at the expense of lower sensitivity, 57% (52-61).

TABLE 8

Sensitivity, specificity, positive predictive value, negative predictive value, and C-statistics for symptoms, signs, and tests for the diagnosis of acute heart failure in the emergency department.

|  | Sensitivity | Specificity | PPV | NPV | C-statistic |
|---|---|---|---|---|---|
| Framingham Major |  |  |  |  |  |
| Paroxysmal nocturnal dyspnea | 52 (47, 57) | 62 (58, 67) | 55 (50, 61) | 59 (54, 63) | 0.57 (0.54, 0.60) |
| Jugular venous distension | 24 (20, 28) | 85 (81, 88) | 58 (50, 66) | 55 (51, 59) | 0.54 (0.51, 0.57) |
| Rales | 60 (55, 65) | 53 (48, 58) | 54 (49, 58) | 60 (55, 64) | 0.57 (0.53, 0.60) |
| CXR Cardiomegaly | 69 (64, 73) | 63 (58, 67) | 63 (58, 67) | 69 (64, 73) | 0.66 (0.63, 0.69) |
| S3 gallop | 12 (9, 16) | 95 (92, 97) | 67 (55, 78) | 54 (51, 58) | 0.53 (0.51, 0.55) |
| Hepatojugular reflux | 9 (6, 12) | 96 (93, 97) | 64 (50, 76) | 54 (50, 57) | 0.52 (0.50, 0.54) |
| CXR pulmonary edema | 55 (50, 60) | 72 (68, 76) | 64 (59, 69) | 64 (60, 68) | 0.64 (0.60, 0.67) |
| Framingham Minor |  |  |  |  |  |
| Lower extremity edema | 70 (65, 74) | 40 (35, 45) | 51 (47, 56) | 59 (54, 65) | 0.55 (0.52, 0.58) |
| Nocturnal cough | 49 (44, 54) | 55 (51, 60) | 50 (45, 55) | 54 (50, 59) | 0.52 (0.49, 0.55) |
| Exertional dyspnea | 94 (91, 96) | 14 (11, 18) | 50 (46, 53) | 71 (60, 80) | 0.54 (0.52, 0.56) |
| Hepatomegaly | 2 (1, 4) | 97 (95, 98) | 39 (20, 62) | 52 (49, 56) | 0.50 (0.48, 0.51) |
| CXR pleural effusion | 28 (23, 32) | 81 (77, 84) | 57 (50, 64) | 55 (51, 59) | 0.54 (0.51, 0.57) |
| Tachycardia | 9 (7, 13) | 87 (84, 90) | 40 (30, 51) | 52 (48, 55) | 0.48 (0.46, 0.50) |
| Framingham HF |  |  |  |  |  |
| 2 major | 82 (79, 86) | 49 (44, 54) | 59 (55, 64) | 76 (70, 81) | 0.66 (0.63, 0.69) |
| 1 major and 2 minor | 11 (8, 15) | 71 (67, 75) | 26 (20, 34) | 47 (43, 51) | 0.41 (0.39, 0.44) |
| Circulating biomarkers |  |  |  |  |  |
| BNP > 100 pg/ml | 97 (95, 99) | 33 (28, 37) | 59 (55, 63) | 93 (87, 97) | 0.65 (0.63, 0.67) |
| Angiopoietin-2 > 228 pg/ml | 76 (72, 80) | 55 (51, 60) | 61 (56, 65) | 72 (67, 77) | 0.66 (0.63, 0.69) |
| Thrombospondin-2 > 33 ng/ml | 73 (68, 77) | 54 (49, 59) | 59 (54, 63) | 69 (64, 74) | 0.64 (0.60, 0.67) |
| Number of positive circulating biomarkers |  |  |  |  | 0.73 (0.70, 0.76) |
| Any 1 | 99 (97, 100) | 24 (21, 29) | 54 (51, 58) | 95 (89, 98) |  |
| Any 2 | 85 (82, 89) | 51 (46, 56) | 61 (57, 65) | 79 (74, 84) |  |
| All 3 | 57 (52, 61) | 76 (72, 80) | 68 (63, 73) | 66 (62, 70) |  |

Figure 4A:
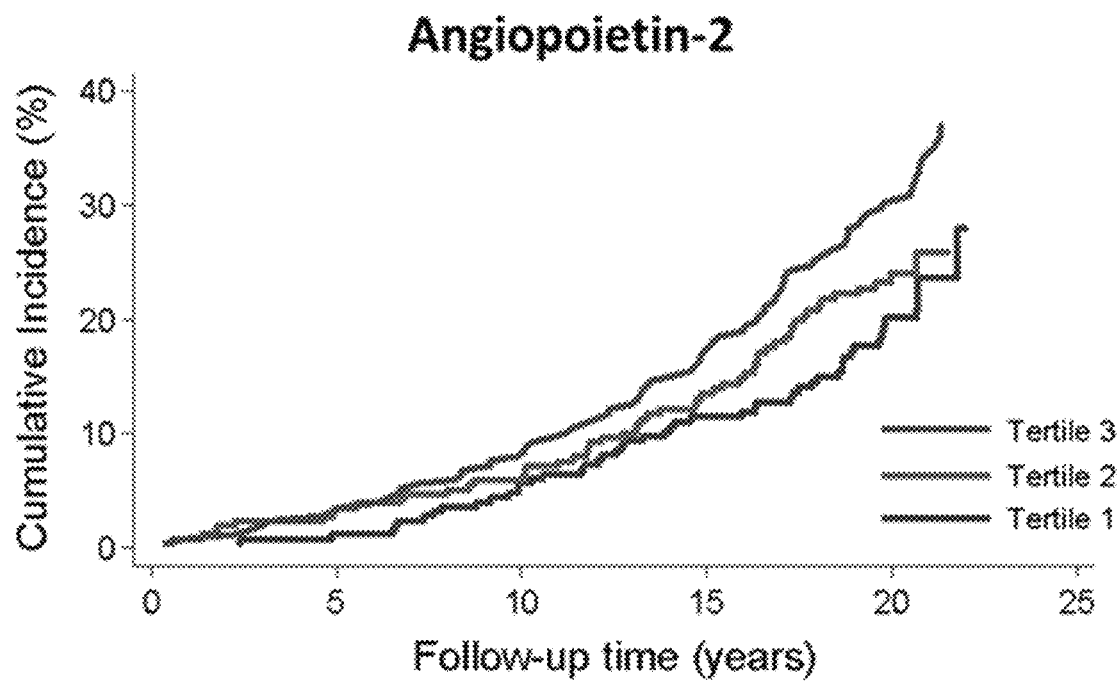
FIGS. 4A and 4B. Cumulative incidence of heart failure according to tertiles of plasma angiopoietin-2 (FIG. 4A) and thrombospondin-2 (FIG. 4B) levels in the Malmo Diet and Cancer Study. Higher plasma levels of both angiopoietin-2 and thrombospondin-2 are associated with greater risk of incident heart failure in the Malmo Diet and Cancer Study.
Figure 4B:
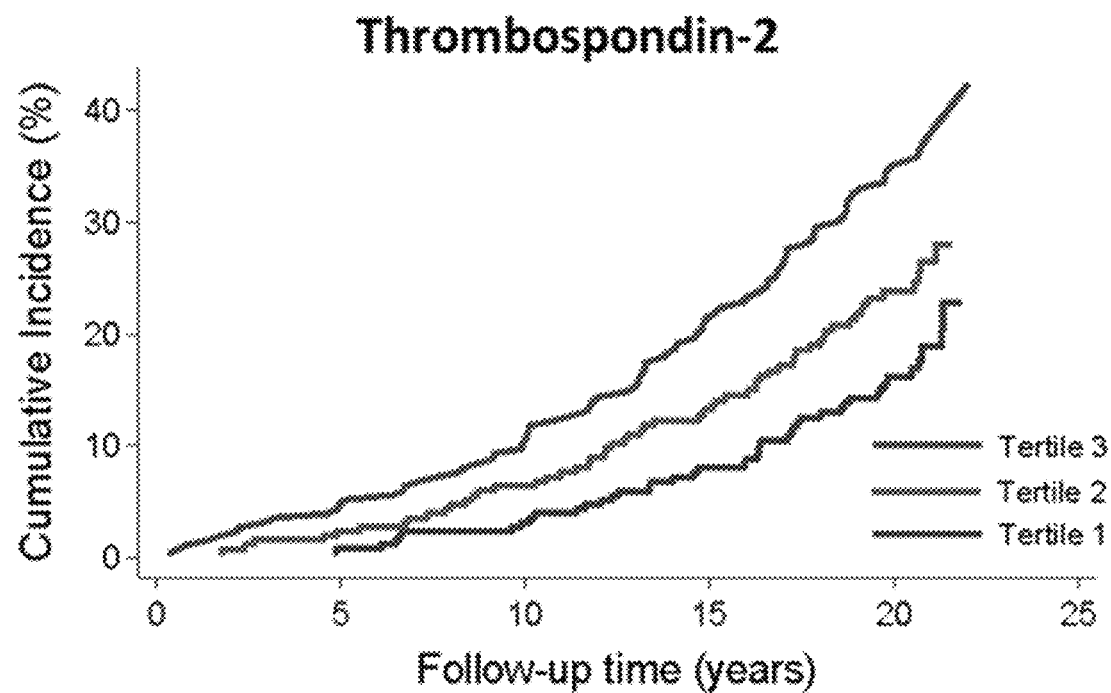

The diagnosis of acute heart failure was adjudicated by an independent group of cardiologists by detailed chart review. PPV=positive predictive value; NPV=negative predictive value; CXR=chest x-ray; HF=heart failure; BNP=B-type natriuretic peptide Biomarker Validation in Longitudinal, Community-Based Study In the MDCS, over a median follow-up of 20.2 years, 185 individuals developed new-onset HF. Characteristics of the 185 individuals with incident HF and 583 randomly sampled population-representative MDCS participants without HF are shown in Table 9. Baseline angiopoietin-2 and thrombospondin-2 levels were higher among individuals that went on to develop HF than those that did not, p<0.001 for both. The risk of HF according to tertiles of each biomarker are shown in FIG. 4.

TABLE 9

Baseline characteristics of individuals with and without incident heart failure in the Malmö Diet and Cancer Study

|  | No Incident Heart Failure N = 583 | Incident Heart Failure N = 185 | P |
|---|---|---|---|
| Age, years | 57 (5.8) | 61 (4.8) | <0.001 |
| Female, % | 59 | 43 | <0.001 |
| Hx of Coronary Artery Disease/MI, % | 2 | 10 | <0.001 |
| Hx of Hypertension, % | 57 | 83 | <0.001 |
| Anti-Hypertensive medication use, % | 15 | 41 | <0.001 |
| Hx of Diabetes Mellitus | 3 | 14 | <0.001 |
| Current smoker, % | 28 | 28 | 1.00 |
| Body mass index, kg/m$^2$ | 25.4 (3.7) | 27.8 (4.5) | <0.001 |
| Systolic BP, mmHg | 139 (18) | 149 (20) | <0.001 |
| Diastolic BP, mmHg | 86 (9) | 90 (9) | <0.001 |
| LDL cholesterol, mg/dL | 4.1 (1.0) | 4.2 (1.0) | 0.74 |
| HDL cholesterol, mg/dL | 1.4 (0.4) | 1.3 (0.4) | <0.001 |
| NTproBNP, pg/ml | 88 (122) | 189 (264) | <0.001 |
| Angiopoietin-2, RFU | 109 (36) | 125 (93) | <0.001 |
| Thrombospondin-2, RFU | 13848 (5023) | 17031 (11444) | <0.001 |

Data presented as percentage or mean (standard deviation). The distribution of continuous variables was compared using Student's t-tests, and for categorical variables using Fisher's exact tests. Hx = history; MI = myocardial infarction; BP = blood pressure; LDL = low density lipoprotein; HDL = high density lipoprotein; NTproBNP = N-terminal pro B-type natriuretic peptide; RFU = refative fluorescence units.

In a Prentice-weighted, multivariable Cox regression adjusted for traditional risk factors and NTproBNP, both biomarkers were associated with risk of incident HF, with hazard ratios per SD biomarker increase of 1.36 (95% CI, 1.13-1.64) for angiopoietin-2, and 1.29 (95% CI, 1.02-1.62) for thrombospondin-2 (Table 10, model 5).

TABLE 10

Associations between angiopoietin-2, thrombospondin-2, and NTproBNP and incident heart failure in the Malmö Diet and Cancer Study

| Model | Covariates | Angiopoietin-2 | Thrombospondin-2 | NTproBNP |
|---|---|---|---|---|
| 1 | Unadjusted | 1.22 (1.16-1.33) | 1.55 (1.36-1.77) | 1.77 (1.52-2.06) |
| 2 | Age, sex | 1.37 (1.17-1.60) | 1.55 (1.39-1.71) | 1.88 (1.50-2.36) |
| 3 | Age, sex, systolic BP, diastolic BP, anti-HTN med use, DM, BMI, LDL, HDL, current smoking, MI | 1.47 (1.23-1.76) | 1.43 (1.10-1.86) | 1.97 (1.52-2.54) |
| 4 | Model 3 + NTproBNP | 1.35 (1.14-1.61) | 1.37 (1.06-1.79) | — |
| 5 | Model 4 + Angiopoietin-2 + Thrombospondin-2 | 1.36 (1.13-1.64) | 1.29 (1.02-1.62) | 1.80 (1.41-2.30) |

Hazard ratios per natural-log transformed standard deviation with 95% confidence intervals are presented.
ANGPT2 = angiopoietin-2; TSP2 = thrombospondin-2; NTproBNP = N-terminal pro B-type natriuretic peptide; BP = blood pressure; HTN = hypertension; DM = diabetes mellitus; BMI = body mass index; LDL = low density lipoprotein; HDL = high density lipoprotein; MI = myocardial infarction.
Model 1 based on unadjusted Cox regression, whereas models 2-5 use Prentice-weighted Cox regression.
Each biomarker was modelled separately in model 1-4 whereas all markers were included in model 5.
C-statistic (95% CI) for clinical model (model 3, but without any of the biomarkers): 0.79 (0.75-0.82).
C-statistic (95% CI) for clinical model plus all 3 biomarkers (model 5): 0.80 (0.77-0.84).

Biomarker Validation in the Advanced HF, Transplant, LVAD Cohort.

Figure 5:
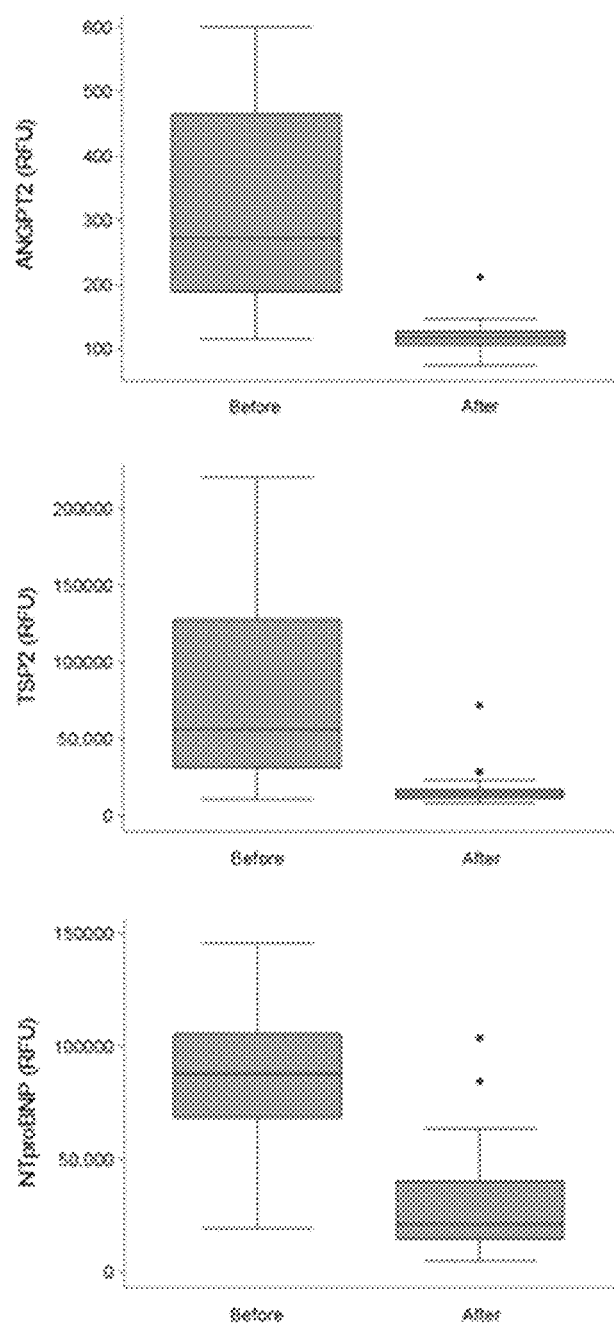
FIG. 5. Angiopoietin-2, thrombospondin-2, and NTproBNP levels in advanced heart failure patients before and after heart transplant. Among advanced heart failure patients undergoing cardiac transplantation (n=30), levels of angiopoietin-2, thrombospondin-2, and NTproBNP are reduced after transplant compared with before transplant, $p<0.001$ for all. ANGPT2=angiopoietin-2, TSP2=thrombospondin-2, NTproBNP=N-terminal pro B-type natriuretic peptide. RFU=relative fluorescence units.

In patients with advanced HF, circulating levels of angiopoietin-2 and thrombospondin-2 were assessed before and after cardiac transplantation (Tables 11 and 12). Transplant was associated with reductions in both angiopoietin-2 (change: −84% [95% CI, −89 to −77]) and thrombospondin-2 (change: −80% [95% CI, −87 to −70]), as well as NTproBNP (change: −72% [95% CI, −80 to −60], p≤0.001 for all (FIG. 5). Levels of both angiopoietin-2 and thrombospondin-2 also decreased after LVAD, p=0.04 for both (FIG. 8).

TABLE 11

Characteristics of advanced heart failure patients prior to heart transplant or left ventricular assist device.

|  | Before heart transplant N = 30 | Before LVAD N = 6 |
|---|---|---|
| Age, years | 51 (10) | 52 (14) |
| Female, n (%) | 7 (23%) | 1 (17%) |
| Ischemic Cardiomyopathy, n (%) | 3 (10%) | 0 (0%) |
| Hypertension, n (%) | 1 (3%) | 1 (17%) |
| Diabetes mellitus, n (%) | 3 (10%) | 0 (0%) |
| Body mass index, kg/m$^2$ | 26.5 (4.4) | 29.2 (6.6) |
| Creatinine, mmol/L | 117 (47) | 138 (50) |
| LVEF, % | 21 (11) | 17 (5) |

Values presented as n (%), or mean (standard deviation). LVAD = left ventricular assist device, LVEF = left ventricular ejection fraction, NTproBNP = N-terminal pro B-type natriuretic peptide.

TABLE 12

Circulating levels of angiopoietin-2, thrombospondin-2, and NTproBNP, before and after heart transplant (n = 30).

|  | Before | After | Percent Change (95% CI) | P-value |
|---|---|---|---|---|
| Angiopoietin-2, RFU | 272 (188-466) | 116 (105-127) | −84 (−89 to −77) | <0.001 |
| Thrombospondin-2, RFU | 56030 (31317-128027) | 14526 (11480-17350) | −80 (−87 to −70) | <0.001 |
| NTproBNP, RFU | 87544 (67943-105620) | 21133 (14326-40500) | −72 (−80 to −60) | <0.001 |

Before and after transplant values presented as median (25$^{th}$-75$^{th}$ percentile). Percent change (95% confidence interval [CI]) from linear mixed models. Serial measures were compared with the Wilcoxon Discussion A pragmatic strategy was developed, which integrating EHRs, automated collection of discarded clinical plasma specimens, and high-throughput proteomics, and applied it to the identification of novel HF biomarkers. The findings highlight the utility of discarded clinical specimens for biomarker discovery, and in doing so, identify angiopoietin-2 and thrombospondin-2 as robust biomarkers of both acute and pre-clinical HF.

Challenges of biomarker studies include the personnel, time, and resources required to collect biospecimens prospectively, especially in acute clinical settings. Although previously-frozen biospecimens are available from clinical trials and epidemiologic cohorts, limitations exist due to selection bias, lack of appropriate clinical context, and finite quantities of stored specimens. The use of discarded blood specimens originally collected for clinical purposes has several advantages. First, it leverages the clinical laboratory infrastructure available at every hospital. Second, it ensures clinical applicability because the biospecimens are collected during the course of actual clinical care. Third, it reduces biases in patient selection or endpoint ascertainment as no investigators are involved in data collection. Fourth, it has the potential to reduce cost without restricting power or generalizability, as the global platform (e.g. proteomics) can be applied to a smaller set of cases and controls from the discarded samples, followed by targeted measurement of selected molecules in larger, well-characterized cohorts.

The effectiveness of this approach is attributable, in part, to the transferability of biomarkers between various clinical settings. For instance, the most frequently measured biomarkers of cardiovascular disease were originally described in acutely ill patients, e.g. C-reactive protein, BNP, and cardiac troponins. Once assays became available to detect the low concentrations of these biomarkers found in ambulatory individuals, each biomarker was validated as a robust predictor of incident disease in apparently healthy people. Thus, hospital-collected specimens should be a reasonable resource for performing initial biomarker screens, provided that specimens from more generalizable cohorts exist for targeted follow-up studies, as in the present investigation.

The findings also suggest that use of real-time EHR algorithms for identification of patients for biomarker studies is pragmatic and efficient. A large number of specimens (>1,000) was accrued in a short time frame (~4 months of active collection). The plasma biobanking methods employed herein could be applied to a wide range of clinical phenotypes, including rare ones, to facilitate biomarker discovery.

Prior examples of biomarker discovery through application of proteomics to discarded clinical samples are lacking. Proteomic methods such as mass spectrometry are presently hampered by low throughput and analytic sensitivity,[3, 4] whereas multiplex platforms such as those utilized in the current study allow simultaneous quantification of hundreds to thousands of proteins at once.[20] Routine clinical laboratory practice and storage conditions of blood samples, i.e. held at 4° C. for ~3 days, may raise concern for analyte degradation. However, circulating peptides are broadly stable in blood samples under these conditions.[16] The feasibility of using discarded clinical blood samples and the potential of high throughput multiplex proteomics is highlighted by the fact that two new biomarkers were identified using only 95 subjects in the initial screen. Thus, by combining automated collection of discarded plasma with a multiplexed proteomic assay, a pragmatic, scalable model for biomarker discovery has been introduced, which is generalizable to a range of clinical phenotypes.

HF is a logical target for biomarker discovery for several reasons. HF is an increasingly common condition, for which accurate and timely diagnosis can be challenging because symptoms and signs overlap those of multiple other conditions. Despite a number of existing HF biomarkers, i.e. natriuretic peptides for excluding the diagnosis of HF, and others such as soluble ST-2, galectin-3, troponin, and cystatin-c, for prognostication, HF remains associated with substantial morbidity and mortality and is a complex syndrome unlikely to be driven by one or a few pathophysiologic mechanisms.[23] There is also an ongoing need for better understanding of the HF syndrome, which can be expedited by biomarker discovery.

Angiopoietin-2 and thrombospondin-2 both have biologically plausible roles in HF. Angiopoietin-2 is an endothelial cell-derived factor linked to the regulation of vascular permeability.[24, 25] Thrombospondin-2 is a fibroblast-derived protein involved in maintaining myocardial matrix integrity in response to increased loading.[26-29] Prior data on the associations of angiopoietin-2 and thrombospondin-2 with HF are limited to a handful of smaller studies; none of which examine these in combination.[30-34] The prognostic association between circulating levels of these proteins and the risk of incident HF has not been previously reported. Nor have prior studies evaluated the diagnostic performance of these biomarkers in acutely symptomatic patients presenting to the ED, where the diagnosis of acute HF is most commonly made. For the first time, it is shown that these two proteins provide additional value for diagnosing acute HF beyond BNP. Finally, the finding that levels of these biomarkers fall after transplantation or LVAD is novel. The consistency of the findings for angiopoietin-2 and thrombospondin-2 across multiple different cohorts for discovery and validation and using different assay techniques (DNA-aptamer based proteomics and conventional immunoassays) lends credence to their robustness as HF biomarkers.

Several study limitations should be acknowledged. As dictated by the unique study design, blood samples were not utilized until they were no longer needed for clinical use (held at 4° C. for three days). Analyte degradation may have led to some false-negative findings, creating a conservative bias. On the other hand, analyte degradation would not explain positive results, such as angiopoietin-2 and thrombospondin-2. This is further supported by validation studies conducted using prospectively-collected plasma specimens that were immediately spun and frozen using standard protocols.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Dieplinger B, Gegenhuber A, Haltmayer M and Mueller T. Evaluation of novel biomarkers for the diagnosis of acute destabilised heart failure in patients with shortness of breath. *Heart*. 2009;95:1508-13.
2. van Kimmenade R R, Januzzi J L, Jr., Ellinor P T, Sharma U C, Bakker J A, Low A F, Martinez A, Crijns H J, MacRae C A, Menheere P P and Pinto Y M. Utility of amino-terminal pro-brain natriuretic peptide, galectin-3, and apelin for the evaluation of patients with acute heart failure. *J Am Coll Cardiol.* 2006;48:1217-24.
3. Lam M P, Ping P and Murphy E. Proteomics Research in Cardiovascular Medicine and Biomarker Discovery. *J Am Coll Cardiol.* 2016;68:2819-2830.
4. Lindsey M L, Mayr M, Gomes A V, Delles C, Arrell D K, Murphy A M, Lange R A, Costello C E, Jin Y F, Laskowitz D T, Sam F, Terzic A, Van Eyk J, Srinivas P R, American Heart Association Council on Functional G, Translational Biology CoCDitYCoCCCoC, Stroke Nursing CoH and Stroke C. Transformative Impact of Proteomics on Cardiovascular Health and Disease: A Scientific Statement From the American Heart Association. *Circulation.* 2015;132:852-72.
5. Smith J G and Gerszten R E. Emerging Affinity-Based Proteomic Technologies for Large-Scale Plasma Profiling in Cardiovascular Disease. *Circulation.* 2017;135:1651-1664.
6. Wells Q S, Veatch O J, Fessel J P, Joon A Y, Levinson R T, Mosley J D, Held E P, Lindsay C S, Shaffer C M, Weeke P E, Glazer A M, Bersell K R, Van Driest S L, Karnes J H, Blair M A, Lagrone L W, Su Y R, Bowton E A, Feng Z, Ky B, Lenihan D J, Fisch M J, Denny J C and Roden D M. Genome-wide association and pathway analysis of left ventricular function after anthracycline exposure in adults. *Pharmacogenet Genomics.* 2017;27: 247-254.
7. Mosley J D, Shoemaker M B, Wells Q S, Darbar D, Shaffer C M, Edwards T L, Bastarache L, McCarty C A, Thompson W, Chute C G, Jarvik G P, Crosslin D R, Larson E B, Kullo I J, Pacheco J A, Peissig P L, Brilliant M H, Linneman J G, Witte J S, Denny J C and Roden D M. Investigating the Genetic Architecture of the PR Interval Using Clinical Phenotypes. *Circ Cardiovasc Genet.* 2017;10.
8. Van Driest S L, Wells Q S, Stallings S, Bush W S, Gordon A, Nickerson D A, Kim J H, Crosslin D R, Jarvik G P, Carrell D S, Ralston J D, Larson E B, Bielinski S J, Olson J E, Ye Z, Kullo I J, Abul-Husn N S, Scott S A, Bottinger E, Almoguera B, Connolly J, Chiavacci R, Hakonarson H, Rasmussen-Torvik L J, Pan V, Persell S D, Smith M, Chisholm R L, Kitchner T E, He M M, Brilliant M R, Wallace J R, Doheny K F, Shoemaker M B, Li R, Manolio T A, Callis T E, Macaya D, Williams M S, Carey D, Kapplinger J D, Ackerman M J, Ritchie M D, Denny J C and Roden D M. Association of Arrhythmia-Related Genetic Variants With Phenotypes Documented in Electronic Medical Records. *JAMA.* 2016;315:47-57.
9. Crawford D C, Crosslin D R, Tromp G, Kullo I J, Kuivaniemi H, Hayes M G, Denny J C, Bush W S, Haines J L, Roden D M, McCarty C A, Jarvik G P and Ritchie M D. eMERGEing progress in genomics-the first seven years. *Front Genet.* 2014;5:184.
10. Bowton E, Field J R, Wang S, Schildcrout J S, Van Driest S L, Delaney J T, Cowan J, Weeke P, Mosley J D, Wells Q S, Karnes J H, Shaffer C, Peterson J F, Denny J C, Roden D M and Pulley J M. Biobanks and electronic medical records:enabling cost-effective research. *Sci Transl Med.* 2014;6:234 cm3.
11. Denny J C, Crawford D C, Ritchie M D, Bielinski S J, Basford M A, Bradford Y, Chai H S, Bastarache L, Zuvich R, Peissig P, Carrell D, Ramirez A H, Pathak J, Wilke R A, Rasmussen L, Wang X, Pacheco J A, Kho A N, Hayes M G, Weston N, Matsumoto M, Kopp P A, Newton K M, Jarvik G P, Li R, Manolio T A, Kullo I J, Chute C G, Chisholm R L, Larson E B, McCarty C A, Masys D R, Roden D M and de Andrade M. Variants near FOXE1 are associated with hypothyroidism and other thyroid conditions:using electronic medical records for genome- and phenome-wide studies. *Am J Hum Genet.* 2011;89:529-42.
12. Roberts E, Ludman A J, Dworzynski K, A1-Mohammad A, Cowie M R, McMurray J J, Mant J and Failure NGDGfAH. The diagnostic accuracy of the natriuretic peptides in heart failure:systematic review and diagnostic meta-analysis in the acute care setting. *BMJ.* 2015;350: h910.
13. York M K, Gupta D K, Reynolds C F, Farber-Eger E, Wells Q S, Bachmann K N, Xu M, Harrell Jr F E and Wang T J. B-Type Natriuretic Peptide Levels and Mortality in Patients With and Without Heart Failure. *J Am Coll Cardiol.* 2018;71:2079-88.
14. Roden D M, Pulley J M, Basford M A, Bernard G R, Clayton E W, Balser J R and Masys D R. Development of a large-scale de-identified DNA biobank to enable personalized medicine. *Clin Pharmacol Ther.* 2008;84:362-9.
15. McGregor T L, Van Driest S L, Brothers K B, Bowton E A, Muglia L J and Roden D M. Inclusion of pediatric samples in an opt-out biorepository linking DNA to de-identified medical records: pediatric BioVU. *Clin Pharmacol Ther.* 2013;93:204-11.
16. Bowton E A, Collier S P, Wang X, Sutcliffe C B, Van Driest S L, Couch L J, Herrera M, Jerome R N, Slebos R J, Alborn W E, Liebler D C, McNaughton C D, Mernaugh R L, Wells Q S, Brown N J, Roden D M and Pulley J M. Phenotype-Driven Plasma Biobanking Strategies and Methods. *J Pers Med.* 2015;5:140-52.
17. Collins S P, Lindsell C J, Jenkins C A, Harrell F E, Fermann G J, Miller K F, Roll S N, Sperling M I, Maron D J, Naftilan A J, McPherson J A, Weintraub N L, Sawyer D B and Storrow A B. Risk stratification in acute heart failure: rationale and design of the STRATIFY and DECIDE studies. *Am Heart J.* 2012;164:825-34.
18. Smith J G, Newton-Cheh C, Almgren P, Struck J, Morgenthaler N G, Bergmann A, Platonov P G, Hedblad B, Engstrom G, Wang T J and Melander O. Assessment of conventional cardiovascular risk factors and multiple biomarkers for the prediction of incident heart failure and atrial fibrillation. *J Am Coll Cardiol.* 2010;56:1712-9.
19. Ingelsson E, Arnlov J, Sundstrom J and Lind L. The validity of a diagnosis of heart failure in a hospital discharge register. *Eur J Heart Fail.* 2005;7:787-91.
20. Gold L, Ayers D, Bertino J, Bock C, Bock A, Brody E N, Carter J, Dalby A B, Eaton B E, Fitzwater T, Flather D, Forbes A, Foreman T, Fowler C, Gawande B, Goss M, Gunn M, Gupta S, Halladay D, Heil J, Heilig J, Hicke B, Husar G, Janjic N, Jarvis T, Jennings S, Katilius E, Keeney T R, Kim N, Koch T H, Kraemer S, Kroiss L, Le N, Levine D, Lindsey W, Lollo B, Mayfield W, Mehan M, Mehler R, Nelson S K, Nelson M, Nieuwlandt D, Nikrad M, Ochsner U, Ostroff R M, Otis M, Parker T, Pietrasiewicz S, Resnicow D I, Rohloff J, Sanders G, Sattin S, Schneider D, Singer B, Stanton M, Sterkel A, Stewart A, Stratford S, Vaught J D, Vrklj an M, Walker J J, Watrobka M, Waugh S, Weiss A, Wilcox S K, Wolfson A, Wolk S K, Zhang C and Zichi D. Aptamer-based multiplexed proteomic technology for biomarker discovery. *PLoS One.* 2010;5:e15004.
21. Ngo D, Sinha S, Shen D, Kuhn E W, Keyes M J, Shi X, Benson M D, O'Sullivan J F, Keshishian H, Farrell L A, Fifer M A, Vasan R S, Sabatine M S, Larson M G, Carr S A, Wang T J and Gerszten R E. Aptamer-Based Proteomic Profiling Reveals Novel Candidate Biomarkers and Pathways in Cardiovascular Disease. *Circulation.* 2016;134:270-85.

22. Benson M D, Yang Q, Ngo D, Zhu Y, Shen D, Farrell L A, Sinha S, Keyes M J, Vasan R S, Larson M G, Smith J G, Wang T J and Gerszten R E. Genetic Architecture of the Cardiovascular Risk Proteome. *Circulation.* 2018; 137:1158-1172.

23. Yancy C W, Jessup M, Bozkurt B, Butler J, Casey D E, Jr., Colvin M M, Drazner M H, Filippatos G S, Fonarow G C, Givertz M M, Hollenberg S M, Lindenfeld J, Masoudi F A, McBride P E, Peterson P N, Stevenson L W and Westlake C. 2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America. *Circulation.* 2017;136:e137-e161.

24. Benest A V, Kruse K, Savant S, Thomas M, Laib A M, Loos E K, Fiedler U and Augustin H G. Angiopoietin-2 is critical for cytokine-induced vascular leakage. *PLoS One.* 2013;8:e70459.

25. Saharinen P, Eklund L, Miettinen J, Wirkkala R, Anisimov A, Winderlich M, Nottebaum A, Vestweber D, Deutsch U, Koh G Y, Olsen B R and Alitalo K. Angiopoietins assemble distinct Tie2 signalling complexes in endothelial cell-cell and cell-matrix contacts. *Nat Cell Biol.* 2008;10:527-37.

26. Papageorgiou A P, Swinnen M, Vanhoutte D, Vanden-Driessche T, Chuah M, Lindner D, Verhesen W, de Vries B, D'Hooge J, Lutgens E, Westermann D, Carmeliet P and Heymans S. Thrombospondin-2 prevents cardiac injury and dysfunction in viral myocarditis through the activation of regulatory T-cells. *Cardiovascular research.* 2012; 94:115-24.

27. van Almen G C, Swinnen M, Carai P, Verhesen W, Cleutjens J P, D'Hooge J, Verheyen F K, Pinto Y M, Schroen B, Carmeliet P and Heymans S. Absence of thrombospondin-2 increases cardiomyocyte damage and matrix disruption in doxorubicin-induced cardiomyopathy. *Journal of molecular and cellular cardiology.* 2011;51:318-28.

28. Swinnen M, Vanhoutte D, Van Almen G C, Hamdani N, Schellings M W, D'Hooge J, Van der Velden J, Weaver M S, Sage E H, Bornstein P, Verheyen F K, VandenDriessche T, Chuah M K, Westermann D, Paulus W J, Van de Werf F, Schroen B, Carmeliet P, Pinto Y M and Heymans S. Absence of thrombospondin-2 causes age-related dilated cardiomyopathy. *Circulation.* 2009;120:1585-97.

29. Schroen B, Heymans S, Sharma U, Blankesteijn W M, Pokharel S, Cleutjens J P, Porter J G, Evelo C T, Duisters R, van Leeuwen R E, Janssen B J, Debets J J, Smits J F, Daemen M J, Crijns H J, Bornstein P and Pinto Y M. Thrombospondin-2 is essential for myocardial matrix integrity: increased expression identifies failure-prone cardiac hypertrophy. *Circulation research.* 2004;95:515-22.

30. Poss J, Ukena C, Kindermann I, Ehrlich P, Fuernau G, Ewen S, Mahfoud F, Kriechbaum S, Bohm M and Link A. Angiopoietin-2 and outcome in patients with acute decompensated heart failure. *Clinical research in cardiology: official journal of the German Cardiac Society.* 2015;104: 380-7.

31. Link A, Poss J, Rbah R, Barth C, Feth L, Selej an S and Bohm M. Circulating angiopoietins and cardiovascular mortality in cardiogenic shock. *Eur Heart* 2013;34:1651-62.

32. Chong A Y, Caine G J, Freestone B, Blann A D and Lip G Y. Plasma angiopoietin-1, angiopoietin-2, and angiopoietin receptor tie-2 levels in congestive heart failure. *J Am Coll Cardiol.* 2004;43:423-8.

33. Chen S, Guo L, Chen B, Sun L and Cui M. Association of serum angiopoietin-1, angiopoietin-2 and angiopoietin-2 to angiopoietin-1 ratio with heart failure in patients with acute myocardial infarction. *Experimental and therapeutic medicine.* 2013;5:937-941.

34. Hanatani S, Izumiya Y, Takashio S, Kimura Y, Araki S, Rokutanda T, Tsujita K, Yamamoto E, Tanaka T, Yamamuro M, Kojima S, Tayama S, Kaikita K, Hokimoto S and Ogawa H. Circulating thrombospondin-2 reflects disease severity and predicts outcome of heart failure with reduced ejection fraction. *Circulation journal:official journal of the Japanese Circulation Society.* 2014;78:903-10.

35. Smith J G, Platonov P G, Hedblad B, Engstrom G, Melander O. Atrial fibrillation in the Malmo Diet and Cancer study: a study of occurrence, risk factors and diagnostic validity. Eur J Epidemiol 2010;25:95-102.

36. Berglund G, Elmstahl S, Janzon L, Larsson S A. The Malmo Diet and Cancer Study. Design and feasibility. J Intern Med 1993;233:45-51.

37. Writing Committee M, Yancy C W, Jessup M, et al. 2013 ACCF/AHA guideline for the management of heart failure: a report of the American College of Cardiology Foundation/American Heart Association Task Force on practice guidelines. Circulation 2013;128:e240-327.

38. Mebazaa A, Yilmaz M B, Levy P, et al. Recommendations on pre-hospital & early hospital management of acute heart failure: a consensus paper from the Heart Failure Association of the European Society of Cardiology, the European Society of Emergency Medicine and the Society of Academic Emergency Medicine. Eur J Heart Fail 2015;17:544-58.

39. Matsue Y, Damman K, Voors A A, et al. Time-to-Furosemide Treatment and Mortality in Patients Hospitalized With Acute Heart Failure. J Am Coll Cardiol 2017;69:3042-51.

40. Wong Y W, Fonarow G C, Mi X, et al. Early intravenous heart failure therapy and outcomes among older patients hospitalized for acute decompensated heart failure:findings from the Acute Decompensated Heart Failure Registry Emergency Module (ADHERE-EM). Am Heart J 2013;166:349-56.

41. Maisel A S, Peacock W F, McMullin N, et al. Timing of immunoreactive B-type natriuretic peptide levels and treatment delay in acute decompensated heart failure: an ADHERE (Acute Decompensated Heart Failure National Registry) analysis. J Am Coll Cardiol 2008;52:534-40.

42. Maisel A, Neath S X, Landsberg J, et al. Use of procalcitonin for the diagnosis of pneumonia in patients presenting with a chief complaint of dyspnoea:results from the BACH (Biomarkers in Acute Heart Failure) trial. Eur J Heart Fail 2012;14:278-86.

43. Schuetz P, Kutz A, Grolimund E, et al. Excluding infection through procalcitonin testing improves outcomes of congestive heart failure patients presenting with acute respiratory symptoms:results from the randomized ProHOSP trial. Int J Cardiol 2014;175:464-72.

44. Maisel A S, Krishnaswamy P, Nowak R M, et al. Rapid measurement of B-type natriuretic peptide in the emergency diagnosis of heart failure. N Engl J Med 2002;347: 161-7.

45. Ledwidge M, Gallagher J, Conlon C, et al. Natriuretic peptide-based screening and collaborative care for heart failure: the STOP-HF randomized trial. JAMA 2013;310: 66-74.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating a subject, comprising:
   (a) determining whether there is angiopoietin-2 (Angpt-2) and/or thrombospondin-2 (Tsp-2) in a blood or plasma sample from the subject by:
      (i) obtaining or having obtained the blood or plasma sample from the subject;
      (ii) performing or having performed an assay to determine whether the sample includes an elevated level of Angpt-2 and/or Tsp-2, wherein it is determined that there is elevated Angpt-2 in the sample when the level of Angpt-2 is above about 220 pg/ml and that there is elevated Tsp-2 in the sample when the level of Tsp-2 is above about 30 ng/ml; and
   (b) if there is an elevated level of Angpt-2 and/or Tsp-2 in the sample, then administering treatment for acute heart failure comprising administering diuretics to the subject.

2. The method of claim 1, wherein the subject has dyspnea.

3. The method of claim 1, and further comprising detecting or having detected natriuretic peptides in the sample.

4. A method of diagnosing and treating acute heart failure in a subject, said method comprising:
   (a) obtaining or having obtained a blood or plasma sample from the subject to detect levels in the sample of one or both of angiopoietin-2 (Angpt-2) and thrombospondin-2 (Tsp-2);
   (c) diagnosing the subject with acute heart failure when there is an elevated level of Angpt-2 and/or Tsp-2 in the sample, wherein it is determined that there is elevated Angpt-2 in the sample when the level of Angpt-2 is above about 220 pg/ml and that there is elevated Tsp-2 in the sample when the level of Tsp-2 is above about 30 ng/ml; and
   (d) administering treatment for acute heart failure comprising administering diuretics to the diagnosed subject.

5. The method of claim 4, wherein the subject has dyspnea.

6. The method of claim 4, and further comprising detecting or having detected natriuretic peptides in the sample.

7. A method of detecting a combination of angiopoietin-2 (Angpt-2) and thrombospondin-2 (Tsp-2) in a sample from a subject, comprising:
   (a) obtaining or having obtained a blood or plasma sample from the subject;
   (b) detecting or having detected Angpt-2 and Tsp-2 in the sample;
   (c) diagnosing the subject with acute heart failure when there is an elevated level of Angpt-2 and/or Tsp-2 in the sample as compared to a non-heart failure control; and
   d) administering treatment for acute heart failure to the subject, said treatment comprising administering diuretics to the subject.

8. The method of claim 7, wherein the subject has dyspnea.

9. The method of claim 7, and further comprising determining that there is an elevated level of Angpt-2 in the sample when the level of Angpt-2 is above about 220 pg/ml and determining that there is an elevated level of Tsp-2 in the sample when the level of Tsp-2 is above about 30 ng/ml.

10. The method of claim 7, and further comprising detecting or having detected natriuretic peptide levels in the sample, and diagnosing the subject with acute heart failure when there is an elevated level of Angpt-2 and/or Tsp-2 as compared to a non-heart failure control, and when the natriuretic peptide levels are above a threshold level for excluding acute heart failure.

11. The method of claim 7, and further comprising identifying the subject as having an increased risk of developing heart failure if there is an elevated level of Angpt-2 and/or Tsp-2 in the sample relative to a non-heart failure control.

12. The method of claim 11, wherein said increased risk is due to the subject having coronary artery disease, myocardial infarction, hypertension, diabetes mellitus, or obesity.

13. The method of claim 11, wherein the treatment further comprises preventing or delaying onset of heart failure when there is an elevated level of Angpt-2 and/or Tsp-2 in the sample as compared to a non-heart failure control.

14. The method of claim 7, and further comprising detecting or having detected natriuretic peptides in the sample, and administering treatment to the subject to prevent or delay onset of heart failure when there is an elevated level of Angpt-2 and/or Tsp-2 relative to a non-heart failure control, and natriuretic peptide levels are above a threshold level for excluding acute heart failure.

\* \* \* \* \*